(12) United States Patent
Pereira et al.

(10) Patent No.: US 11,864,736 B2
(45) Date of Patent: Jan. 9, 2024

(54) AUTOMATED FLUID MANAGEMENT SYSTEM

(71) Applicant: BOSTON SCIENTIFIC SCIMED, INC., Maple Grove, MN (US)

(72) Inventors: Peter J. Pereira, Mendon, MA (US); Mayur Kiran Patel, Framingham, MA (US); William Stanhope, Lunenburg, MA (US); Eric Wong, South Grafton, MA (US); Jozef Slanda, Milford, MA (US); Christopher P Gauvin, South Grafton, MA (US); Chad Schneider, Owings Mills, MD (US); Brandon W. Craft, Edgewater, MD (US); Kimberly DeGraaf, Holden, MA (US); Brian P. Watschke, Minneapolis, MN (US); Timothy Paul Harrah, Cambridge, MA (US); Niraj Prasad Rauniyar, Plymouth, MN (US); Sacha Tang, Wilmington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 832 days.

(21) Appl. No.: 15/985,352

(22) Filed: May 21, 2018

(65) Prior Publication Data
US 2018/0361055 A1    Dec. 20, 2018

Related U.S. Application Data

(60) Provisional application No. 62/570,990, filed on Oct. 11, 2017, provisional application No. 62/521,898, filed on Jun. 19, 2017.

(51) Int. Cl.
*A61B 1/015* (2006.01)
*A61B 1/00* (2006.01)
(Continued)

(52) U.S. Cl.
CPC ........ *A61B 1/015* (2013.01); *A61B 1/000095* (2022.02); *A61M 1/77* (2021.05);
(Continued)

(58) Field of Classification Search
CPC ... A61B 1/00009; A61B 1/05; A61B 1/00045; A61B 1/00039; A61B 1/0008;
(Continued)

(56) References Cited

U.S. PATENT DOCUMENTS

| 4,998,914 A | 3/1991 | Wiest et al. |
|---|---|---|
| 6,159,160 A | 12/2000 | Hsei et al. |

(Continued)

FOREIGN PATENT DOCUMENTS

| CN | 105377159 | 3/2016 |
|---|---|---|
| JP | S63230142 | 9/1998 |

(Continued)

*Primary Examiner* — Kevin C Sirmons
*Assistant Examiner* — Avery Smale
(74) *Attorney, Agent, or Firm* — Bookoff McAndrews, PLLC

(57) ABSTRACT

A fluid management system includes a pump configured to pump fluid through the system at a fluid flow rate. The system includes a processor including a user interface, the user interface allowing a user to input a set of system operating parameters, the processor being configured to control the pump to maintain a target fluid flow rate based on the set of system operating parameters. The system further includes a scope device coupled to the pump to deliver the fluid to a target surgical site, the scope device including an elongated shaft extending from a distal end thereof, the elongated shaft including at least one sensor, the at least one sensor transmitting sensor data relating to the target surgical site to the processor. The processor automatically signals to the pump to adjust the fluid flow rate based on the sensor data.

17 Claims, 26 Drawing Sheets

(51) Int. Cl.
*A61M 1/00* (2006.01)
*A61M 5/44* (2006.01)
*A61M 5/14* (2006.01)
*A61B 1/307* (2006.01)

(52) U.S. Cl.
CPC ......... *A61B 1/0004* (2022.02); *A61B 1/00042* (2022.02); *A61B 1/00045* (2013.01); *A61B 1/307* (2013.01); *A61M 5/1414* (2013.01); *A61M 5/445* (2013.01); *A61M 2205/127* (2013.01); *A61M 2205/18* (2013.01); *A61M 2205/3334* (2013.01); *A61M 2205/3344* (2013.01); *A61M 2205/3368* (2013.01); *A61M 2205/3393* (2013.01); *A61M 2205/502* (2013.01)

(58) Field of Classification Search
CPC . A61B 1/00112; A61B 1/00131; A61B 1/015; A61B 1/126; A61B 1/000095; A61B 1/00097; A61B 1/00163; A61B 1/005; A61B 1/04; A61B 1/051; A61B 1/307; A61M 3/0258; A61M 3/0216; A61M 3/022; A61M 1/0058; A61M 2205/3334; A61M 2205/127; A61M 2205/3344; A61M 2205/18; A61M 2205/3393; A61M 2205/3368; A61M 3/0254; A61M 5/1414; A61M 2025/0001; A61M 2025/0002; A61M 2039/0009; A61M 2205/3306; A61M 25/0082; A61M 2205/0216; A61M 2210/1433; A61M 1/73; A61M 1/77; A61M 5/14; A61M 5/142; A61M 5/16877; A61M 5/172; A61M 5/1723; A61M 2005/1726; A61M 5/44; A61M 2205/3327; A61M 2205/3331; A61M 2205/3379; A61M 2205/36; A61M 2205/50; A61M 2205/502
See application file for complete search history.

(56) References Cited

U.S. PATENT DOCUMENTS

| | | | |
|---|---|---|---|
| 9,138,134 B2 * | 9/2015 | Finkman | A61B 1/3137 |
| 2010/0228222 A1 | 9/2010 | Williams et al. | |
| 2011/0144429 A1 * | 6/2011 | Finkman | A61B 1/00091 |
| | | | 600/156 |
| 2013/0267892 A1 * | 10/2013 | Woolford | A61M 3/0258 |
| | | | 604/34 |
| 2013/0331730 A1 * | 12/2013 | Fenech | A61B 1/00091 |
| | | | 600/560 |
| 2014/0303551 A1 | 10/2014 | Germain et al. | |
| 2016/0331888 A1 * | 11/2016 | Koolbergen | A61M 3/0204 |
| 2017/0000946 A1 | 1/2017 | Boyle et al. | |

FOREIGN PATENT DOCUMENTS

| | | |
|---|---|---|
| JP | 2016501110 | 1/2016 |
| WO | 2012/035923 | 3/2012 |

* cited by examiner

AUTOMATED FLUID MANAGEMENT SYSTEM

PRIORITY CLAIM

The present disclosure claims priority to U.S. Provisional Patent Application Ser. No. 62/521,898 filed Jun. 19, 2017 and U.S. Provisional Patent Application Ser. No. 62/570,990 filed Oct. 11, 2017; the disclosures of which are incorporated herewith by reference.

BACKGROUND

Flexible ureteroscopy (fURS) procedures require the circulation of fluid for several reasons. Surgeons today deliver the fluid in various ways such as, for example, by hanging a fluid bag and using gravity to deliver the fluid, filling a syringe and manually injecting the fluid or using a peristaltic pump to deliver fluid from a reservoir at a fixed pressure or flow rate. The deficiency in these and other delivery methods is that the user is not fully aware of what the pressure collecting system or anatomy (ureter, bladder, kidneys) is experiencing, which increases the risk of harming the patient. Conservative surgeons generally circulate fluid at low pressure. However, reducing the flow rate to keep the pressure down may directly affect the visualization of the surgical field because blood, clots and particulate matter may not be sufficiently cleared at low pressure. In contrast, a high perfusion flow rate may get the desired clear visibility but may result in too high an intraluminal pressure. High intraluminal pressure makes it easy for bacterial and endotoxins to be absorbed into the blood which may result in postoperative fever. Other situations that may occur due to high intraluminal pressure include lymph node and venous reflux causing fluid leakage, postoperative pain, urosepsis and renal injury.

SUMMARY

The present disclosure relates to a fluid management system. The system includes a pump configured to pump fluid from a fluid supply source through the system at a fluid flow rate, a processor including a user interface, the user interface allowing a user to input a set of system operating parameters, the processor being configured to control the pump to maintain a target fluid flow range based on the set of system operating parameters, and a scope device coupled to the pump to deliver fluid to a target surgical site, the scope device including an elongated shaft extending from a distal end thereof, the elongated shaft including at least one sensor, the sensor transmitting sensor data relating to target surgical site to the processor, wherein the processor automatically signals to the pump to adjust the fluid flow rate based on the sensor data.

In an embodiment, the sensor is a pressure transducer.

In an embodiment, the system includes a heating assembly, the heating assembly configured to heat the fluid to a target temperature.

In an embodiment, the processor further includes a display screen configured to display the fluid flow rate and sensor data in real time.

In an embodiment, if the processor detects that the fluid flow rate is outside of the target fluid flow range, a visual alert is displayed on the display screen.

In an embodiment, the scope device further includes a temperature sensor located on the elongated shaft.

In an embodiment, the fluid supply source is a fluid bag.

In an embodiment, the system includes a weight sensor for measuring the weight of the fluid bag in real time.

The present disclosure also relates to a fluid management system. The system includes a pump configured to pump fluid from a fluid supply source through the system at a fluid flow rate, a processor configured to control the pump, and a scope device coupled to the pump to deliver fluid to a target surgical site, the scope device including an elongated shaft extending from a distal end thereof, the elongated shaft including a camera, the camera transmitting video feedback relating to target surgical site to the processor, wherein the processor includes image recognition software to detect variations in the video feedback and automatically signals to the pump to adjust the fluid flow rate based on the variations.

In an embodiment, the processor includes a user interface allowing a user to input a set of system operating parameters.

In an embodiment, the processor includes a display screen configured to display the video feedback and the flow rate in real time.

In an embodiment, the scope device further includes a temperature sensor located on the elongated shaft.

In an embodiment, the system includes a heating assembly, the heating assembly configured to heat the fluid to a target temperature.

In an embodiment, the fluid supply source is a fluid bag.

In an embodiment, the device includes a weight sensor for measuring the weight of the fluid bag in real time.

BRIEF DESCRIPTION

DETAILED DESCRIPTION

Figure 1:
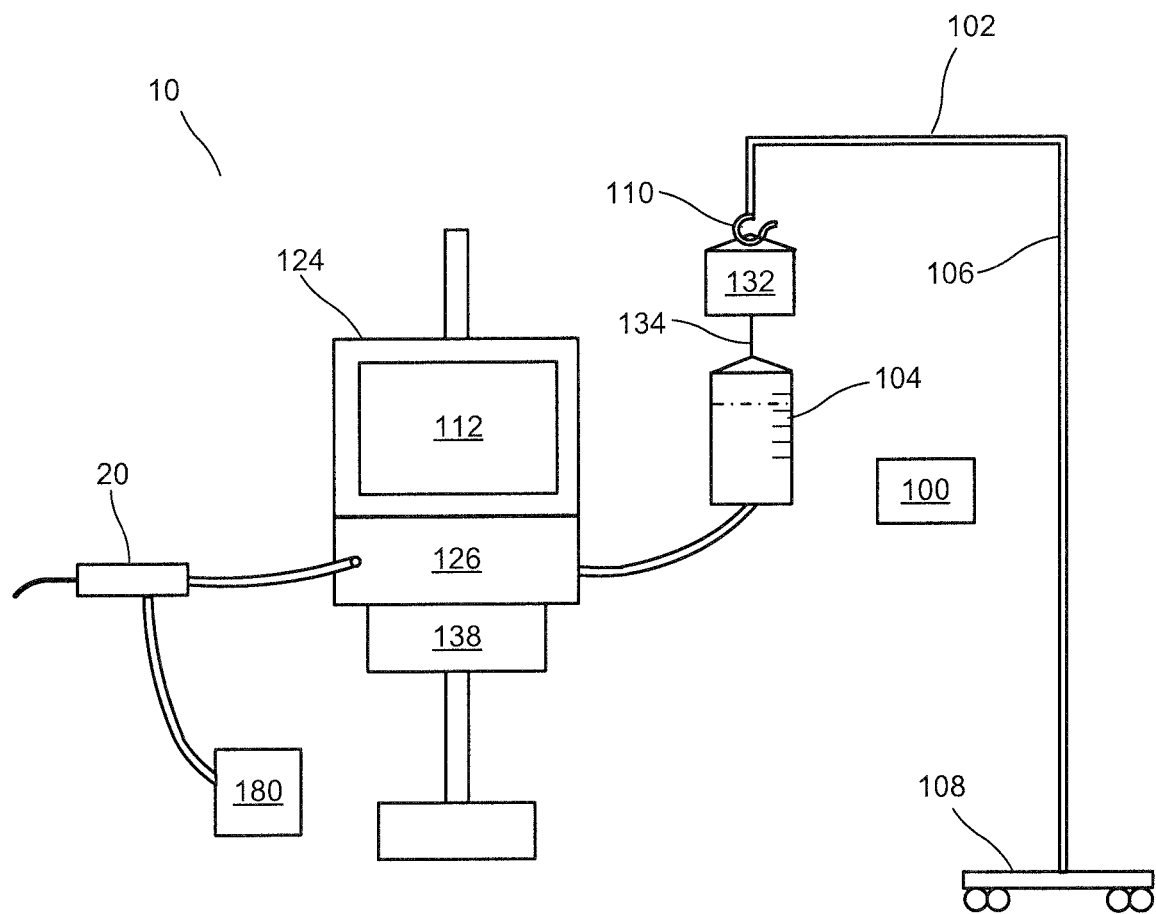
FIG. 1 is a schematic illustration of a fluid management system according to an exemplary embodiment of the present disclosure.

The present invention may be understood with respect to the following description and the appended drawings, wherein like elements are referred to with the same reference numerals. The present invention relates to a systems, methods, devices, and kits for the delivery of fluid in fURS procedures through controlled flow rate and sensor feedback. Exemplary embodiments describe a modular system including a pump which is either user controlled or automated, a ureteroscope device such as, for example, a LithoVue™ scope device with sensors at the tip, a fluid management system and, in some embodiments, a drainage collection system. The pump system may include a heating source to head the fluid to body temperature if desired by the user. Other exemplary embodiments describe a fluid management system kit which may comprise any combination of any two or more of an irrigation tubing, a tool with a pressure or temperature sensor, a drainage canister and printed material with one or more of storage information and instructions regarding how to set up irrigation tubing. It should be noted that the terms "proximal" and "distal" as used herein are intended to refer to a direction toward (proximal) and away from (distal) a user of the device.

Figure 2:
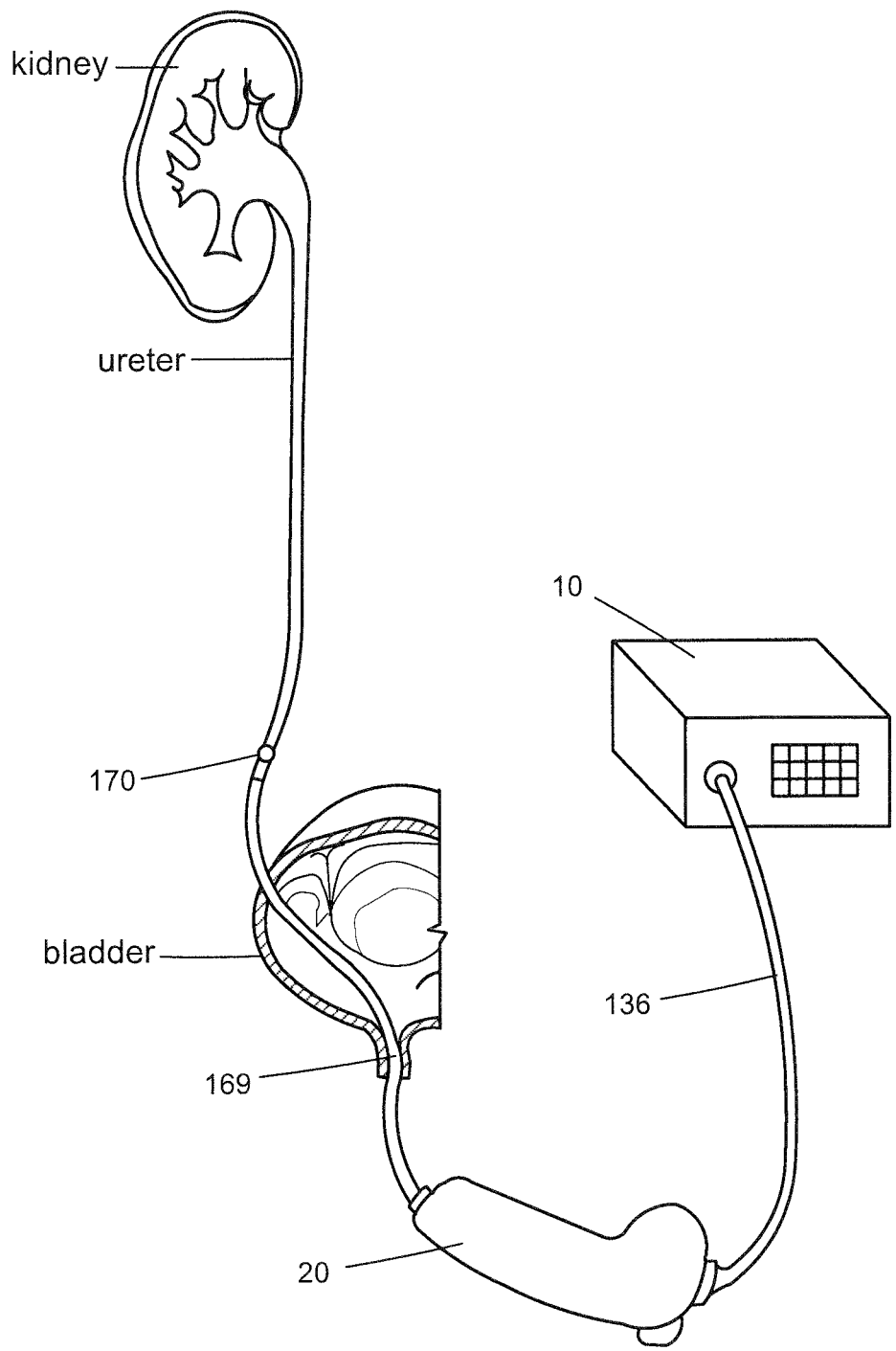
FIG. 2 is another schematic illustration of the fluid management system of FIG. 1 according to an exemplary embodiment of the present disclosure.
Figure 3:
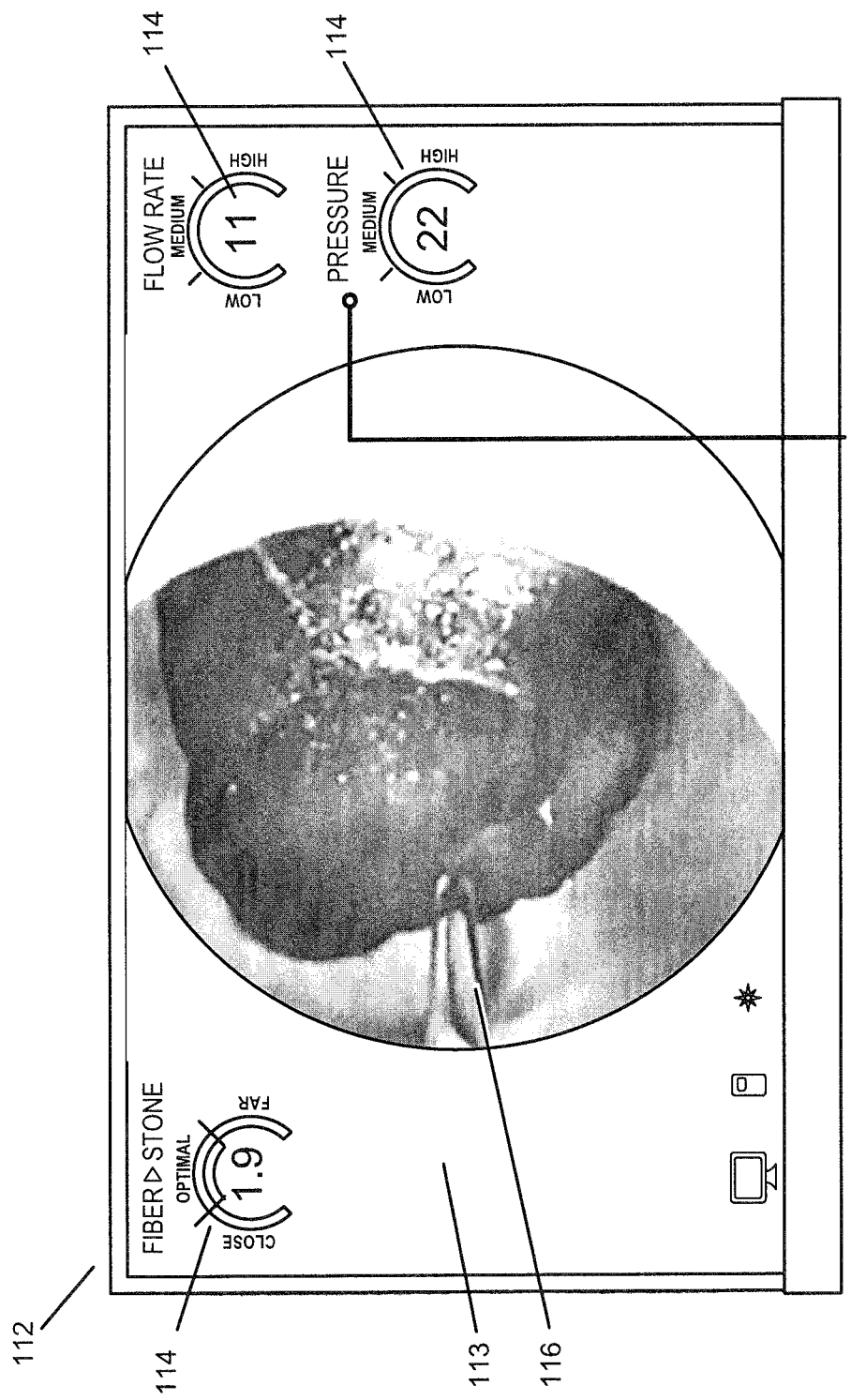
FIG. 3 shows a touch screen interface of the system of FIG. 1 according to a first exemplary embodiment.

FIGS. 1-2 illustrate an exemplary modular fluid management system 10. Fluid management system 10 may be coupled to a surgical device that allows flow of fluid therethrough and includes a pressure sensor such as, for example, a LithoVue™ scope device 20. In an exemplary embodiment, the device 20 also includes a temperature sensor to provide temperature feedback to the system 10 and/or a camera to provide visual feedback to the fluid management system 10. The fluid management system 10 also includes a fluid hanger module 100. An exemplary fluid hanger module 100 may include one or more fluid container supports, such as fluid bag hangers 102, each of which supports one or more fluid bags 104. In an embodiment, placement of the fluid bag 104 may be detected using a remote sensor. The fluid bag hangers 102 may receive a variety of sizes of fluid bags 104 such as, for example, 1 liter (L) to 5 L bags. It will be understood that any number of fluid containers may be used. Furthermore, fluid containers of any size may be used depending on the procedure. An exemplary fluid management unit 100 may be mounted to a rolling stand, which may include a pole 106 and/or base 108. Base 108 may include a plurality of wheels to facilitate easy movement of the fluid management unit 100 when in use. However, it will be understood that fluid bag 104 may also be hung from the ceiling or in between depending on the clinical preference. A fluid bag hanger 102 extends from the pole 106 and may include one or more hooks 110 from which one or more fluid bags 104 may be suspended. Fluid used in the fluid management system 100 may be 0.9% saline. However, it will be understood that a variety of other fluids of varying viscosities may be used depending on the procedure.

The fluid management system 10 may also include one or more user interface components such as a touch screen interface 112. The touch screen interface 112 includes a display screen 113 and may include switches or knobs in addition to touch capabilities. The touch screen interface 112 allows the user to input/adjust various functions of the system 10 such as, for example flow rate, pressure or temperature. The user may also configure parameters and alarms (such as max pressure alarm), information to be displayed and the procedure mode. The touch screen interface 112 allows the user to add, change or discontinue the use of various modular systems within the fluid management system 10. The touch screen interface 112 may also be used to change the system 10 between automatic and manual modes for various procedures.

Figure 4:
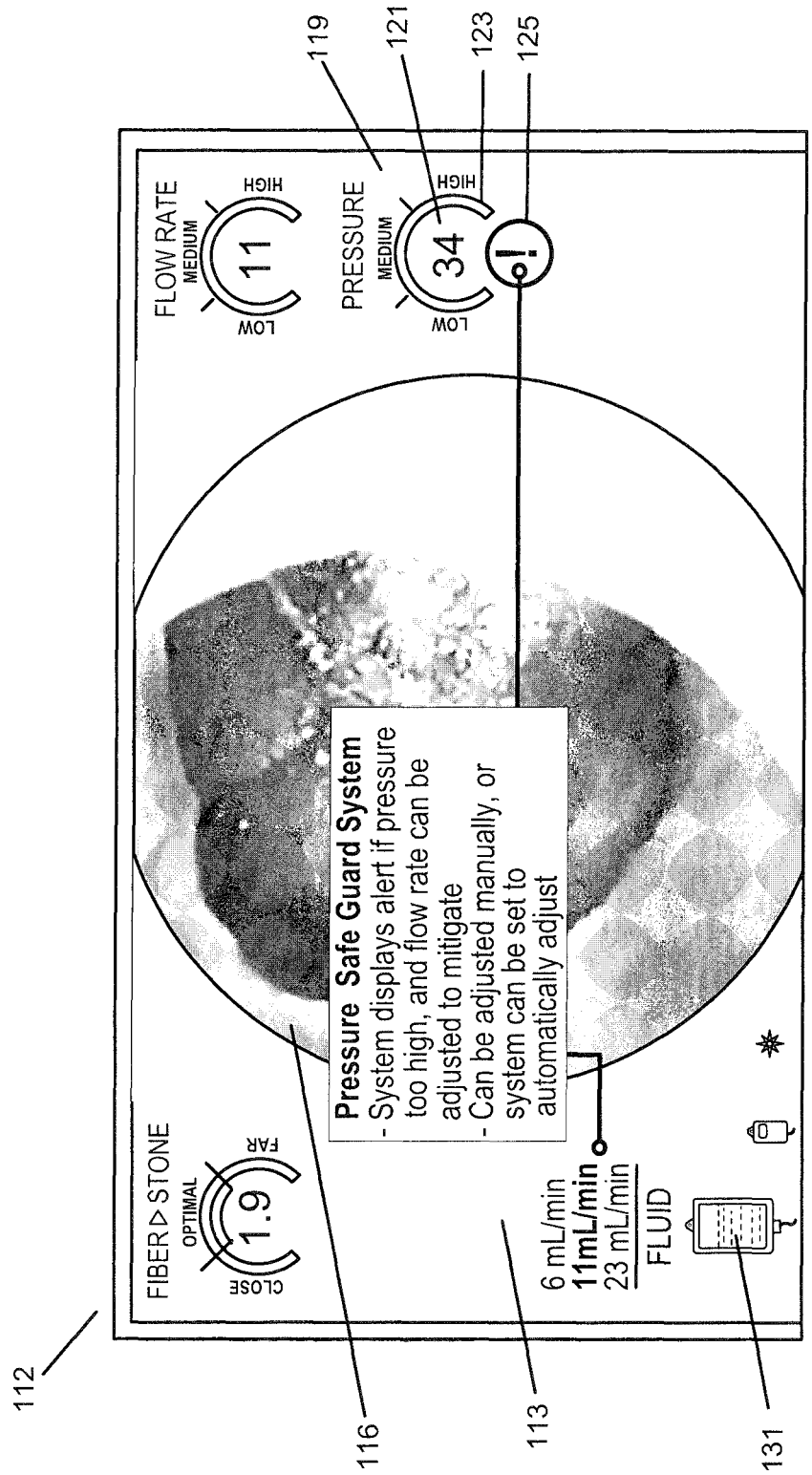
FIG. 4 shows a touch screen interface of the system of FIG. 1 according to a second exemplary embodiment.
Figure 5:
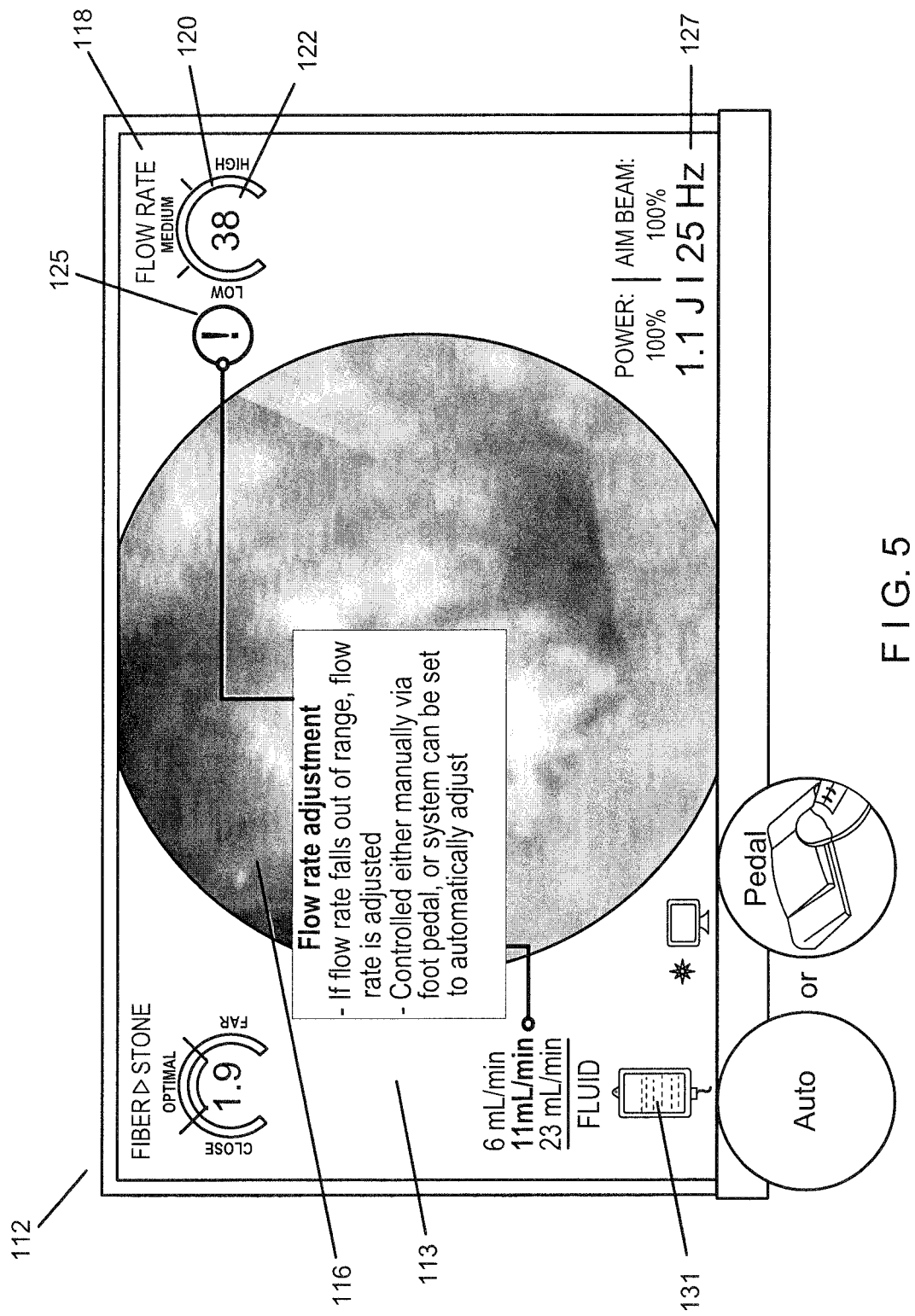
FIG. 5 shows a touch screen interface of the system of FIG. 1 according to a third exemplary embodiment.

FIGS. 3-6 show an exemplary touch screen interface 112. Portions of the touch screen interface 112 may be configured to appear like buttons and/or may provide a functionality similar to physical buttons as would be understood by those skilled in the art. The display screen 113 may be configured to show icons 114 related to modular systems and devices included in the fluid management system 10. For example, in FIG. 3 the display screen 113 provides the user with a live video feed 116 of the target tissue/vessel/cavity from the scope or medical device 20. The display screen 113 may also include a flow rate display 118, as shown in FIG. 5. The flow rate display 118 may be determined based on a desired threshold for flow rate set by the user prior to the procedure or based on known common values, etc. In some embodiments, the operating parameters may be adjusted by touching the corresponding portion of the touch screen interface 112. The exemplary flow rate display 118 then provides a flow rate scale 120 with, for example, distinct low, medium and high ranges based on the operating parameters input by the user as well as the actual flow rate 122. In real time, the flow rate display 118 adjusts both the actual flow rate 122 and the rate marker on the flow rate scale 120. If the flow rate enters the high range, a visual alert 125 and/or audio alarm may in this embodiment be automatically actuated, as illustrated in FIG. 5. As shown in FIG. 4, a similar pressure display 119 may be provided on the display screen 113. Again, the pressure scale 123 may be determined based on parameters previously input by the user or by known common values. The display screen 113 may also display the actual pressure 121 in real time. In other embodiments, the display screen 113 may also show the system power 127, the amount of fluid remaining in the fluid bag 131, and any other information the user may find useful during the procedure, as can be seen in FIG. 5.

In an exemplary embodiment, the fluid management system 100 also includes further user interface components such as a foot pedal 117, heater interface 168, fluid control interface 127 or other device to manually control various modular systems. For example, foot pedal 117 may be used to manually control flow rate.

The touch screen interface 112 is operatively connected to or integrally a part of a main processing device 124 such as a computer. The main processing device 124 may be operatively connected to one or more system components such as, for example, a pump assembly, a heating assembly and a fluid deficit management system. The main processing device 124 is capable of performing various functions such as calculation, control, computation, display, etc. The main processing device 124 is also capable of tracking and storing data pertaining to the operations of the management system 10 and each component thereof. In an exemplary embodiment, the main processing device 124 includes network communication capabilities, such as WiFi, through which the device may be connected to, for example, a social area network. The main processing device 124 may also receive signals from the sensors of the system 10. In an embodiment, the main processing 124 may communicate with databases for best practice suggestions and the maintenance of patient records which may be displayed to the user on the display screen 113.

The fluid management system 10 may be user selectable between different modes based on the procedure, patient characteristics, etc. For example, different modes may include—i.e., fURS Mode, BPH Mode, Hysteroscopy Mode, Cystoscopy Mode. Once a mode has been selected by the user, mode parameters such as flow rate, pressure, fluid deficit and temperature are provided to the user via the display screen. The exemplary parameters of the specific modes may be previously determined and loaded onto the main processing device 124 using, for example, software. Thus, when a user selects a procedure from an initial display on the touch screen interface display screen 113, these known parameters are loaded from the processor to the various components of the fluid management system—i.e., pump, heating assembly, fluid deficit management system. The fluid management system 10 may also be user selectable between automatic and manual mode. For example, for certain procedures, the user may wish to manually adjust a flow rate, pressure or other parameters. Once the user has selected the manual mode on, for example, the touch screen interface 112, the user may the adjust flow rate or pressure via other manual interfaces such as foot pedal 117 or fluid control interface 127.

Figure 7:
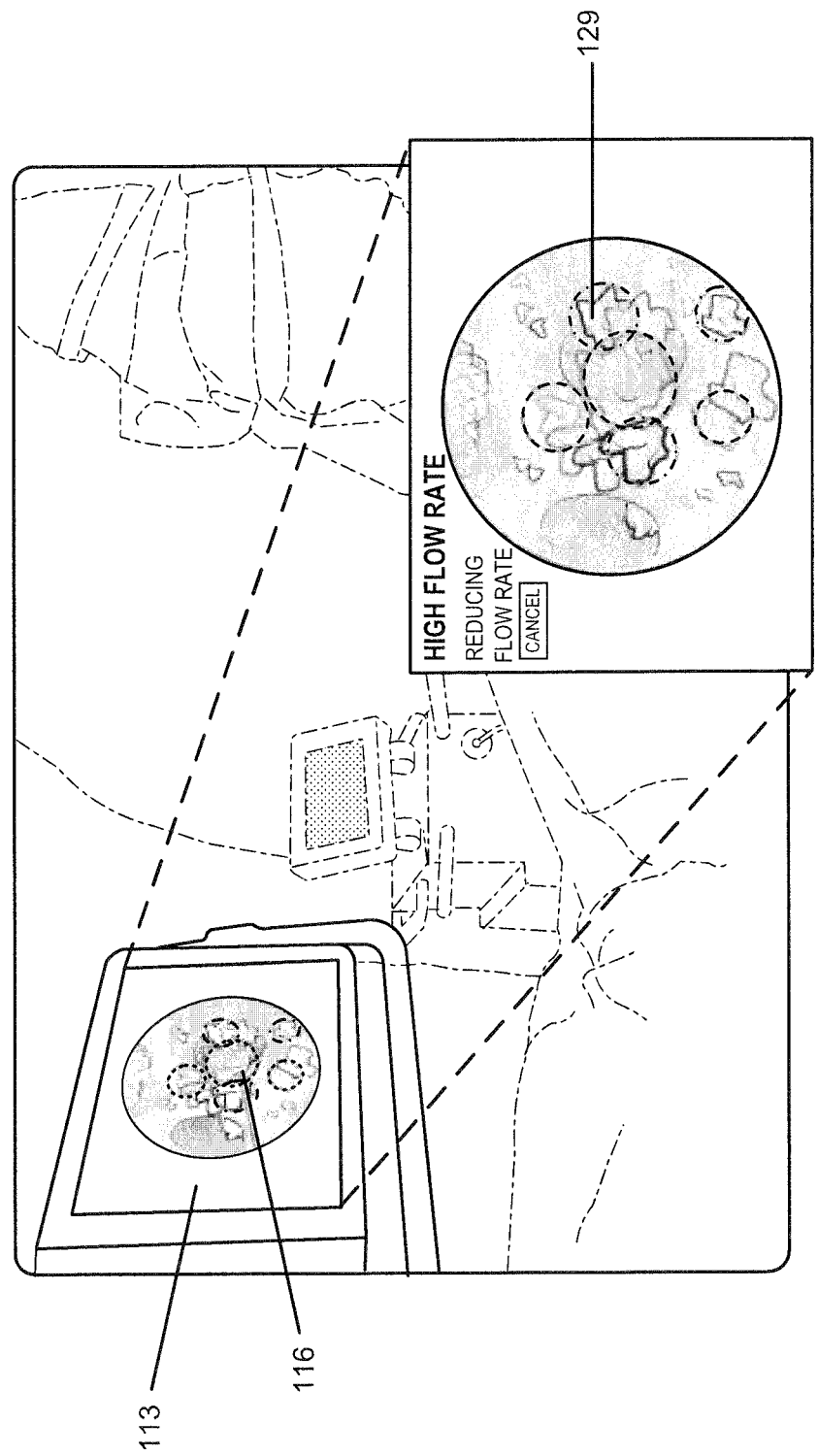
FIG. 7 shows a visual feedback display of the system of FIG. 1 according to an exemplary embodiment.
Figure 8:
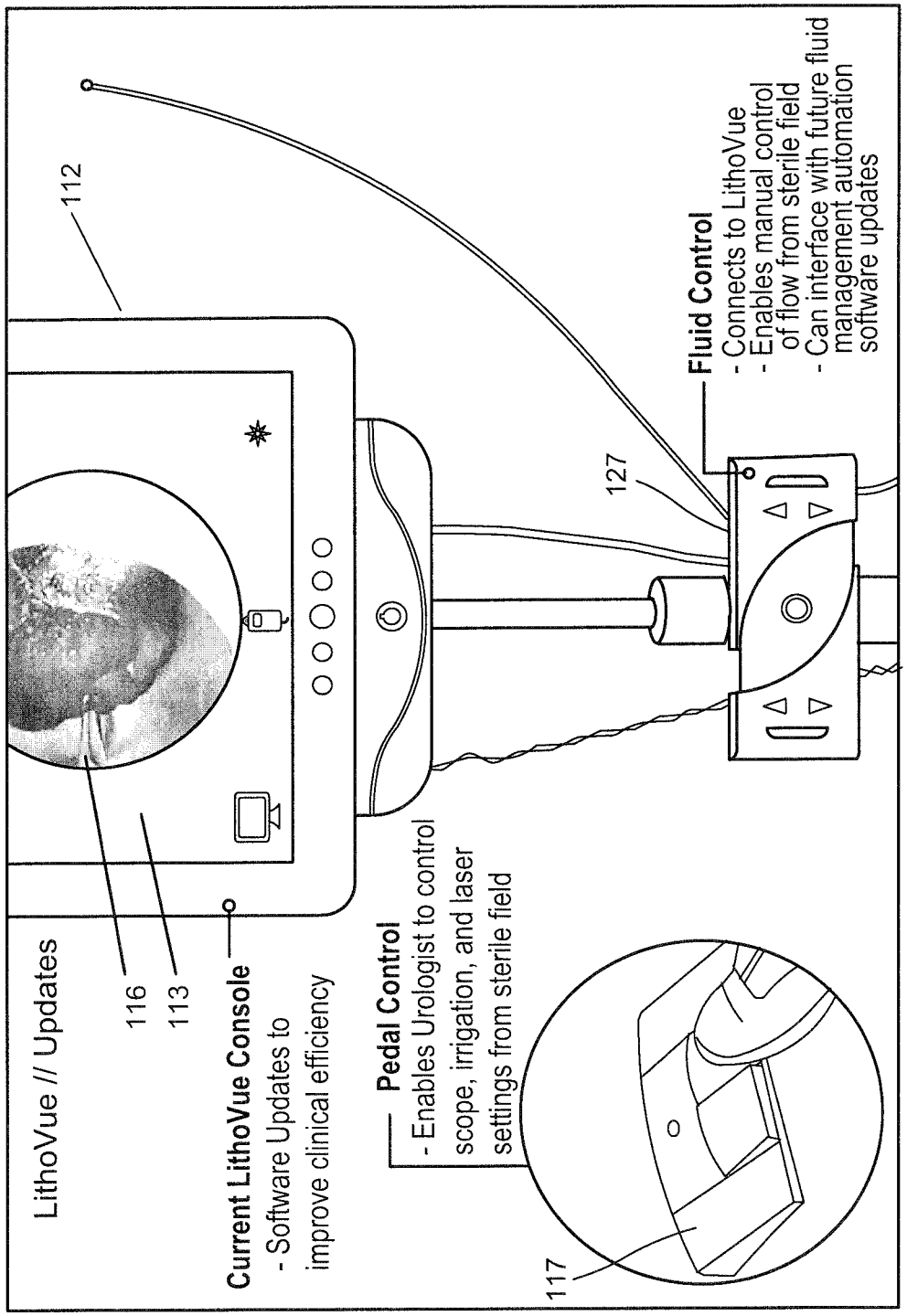
FIG. 8 shows a perspective view of various manual user interfaces of the system of FIG. 1 according to an exemplary embodiment.

The main processing device 124 may be configured to include visual software/image recognition software that can detect visual noise based on variations in brightness (i.e., light monitoring), contrast, or color pixilation. If the image provided to the main processing device 124 is determined to be not sufficiently clear or sharp, the fluid management system 10 increases the flow rate of the fluid to flush out debris 129 to sharpen/clear the image. The flow rate is increased for a temporary time (i.e., a predetermined time period) or until the field of view is deemed to be sufficiently clear. This temporary increase ensures that the time at which a flow rate is increased is limited to ensure that pressure does not exceed safe limits. For example, the system 10 may recognize a red hue, as shown in FIG. 7 in the irrigation (a sign of blood) and signal to a set of peristaltic pumps 126 to increase the flow rate until the blood is cleared from the field of view. Alternatively, the processor may provide a visual alert on the display screen 113 or an audible alert to the physician or nurse that a cloudy view has been detected and the user may then adjust the irrigation flow rate manually. In another example, in instances where there is a lot of debris, light reflected from the debris will brighten the image substantially. In this situation, the main processing device 124 detects this inordinate brightness and signals to the pumps 126 to increase a flow rate to remove debris. Once the reflected light has been reduced as the debris is flushed clear of the field of view of the vision system, the pumps 126 are controlled by the main processing device 124 to reduce the flow rate. Preferably, the physician may create a baseline level for visibility at which he or she prefers to initiate a field clearing flow of fluid and input these parameters into the system 10 via the touch screen interface 112 prior to the procedure. Once the baseline has created, the system 10 monitors the visual feed for variation in the picture and adjusts the flow rate as necessary.

In order to adjust the rate of flow of fluid through the system 10, fluid management unit 100 may include one or more pressurization devices such as a pump 126. An exemplary pump 126 may be a peristaltic pump. The pump 126 may be electrically driven and may receive power from a line source such as a wall outlet or an external or internal electrical storage device such as a disposable or rechargeable battery. The peristaltic pump 126 may operate at any desired speed sufficient to deliver fluid at a target pressure such as, for example, 5 mmHg to 50 mmHg. As noted previously, the pump 126 may be automatically adjusted based on, for example, pressure and temperature readings within the patient and visual feedback from the scope 20. The pump 126 may also be manually adjusted via, for example, foot pedal 117, the touch screen interface 112, or a separate fluid controller 127 (as shown in FIG. 4). The fluid controller 127 may be a separate user interface including buttons that allow the user to increase or decrease each individual pump 126. It will be understood that any number of pumps may be used. In an embodiment, the system 10 may include multiple pumps having different flow capabilities. Flow meter located before or after the pump.

In this embodiment, the flow rate of the fluid at any given time is displayed on the display screen 113 to allow the operation room (OR) visibility for any changes. If the OR personnel notice a change in flow rate that is either too high or too low, the user may manually adjust the flow rate back to a preferred level. This may happen, for example, as physicians insert and remove tools into the working channel of the scope 20. The system 10 may also monitor and automatically adjust the flow rate based on previously set parameters, as previously discussed. This feature may also be beneficial when flow is provided manually such as an assistant injecting irrigation through a syringe.

As noted above, in an embodiment, the system 10 may include visual software or image recognition and analysis software. In this embodiment, the system 10 may detect, via a camera 128 positioned on the scope 20 within the body, whether a tool has been inserted or not and which tool is being used. The tool may, for example, have an identifiable marker that the visual software may see to inform the system what type of tool is being used. The fluid management system 10 may then automatically adjust the flow rate based on the tool identified by the visual software. When the tool is retracted from the working channel, the fluid management system 10 reduces the pump rate accordingly.

In another embodiment, the system 10 automatically adjusts the flow rate based on a pressure and/or a temperature detected within the patient. The pressure and/or the temperature may be measured in line through a tool, such as the scope 20, used in conjunction with the system 10. The system 10 may include pressure monitoring software so that the pump 126 may be configured by the user to be automatically started, stopped, and/or speed adjusted by the system 10 to maintain a fluid pressure delivered to a surgical site at a target pressure and/or within a predetermined pressure band. For example, a scope pressure sensor may detect pressure within the kidney and automatically alter the flow rate within the system 10 based on a monitored intrarenal pressure. If intrarenal pressure is too high, the system 10 will decrease the flow rate and vice versa. In an exemplary temperature control mode, system 10 may include temperature monitoring software so that a heater may be controlled (e.g., started, stopped, and temperature adjusted) to maintain a fluid temperature delivered to a surgical site at about a target temperature and/or within a predetermined temperature pressure band, as will be described in further detail below. For example, temperature may be monitored in vivo or in vitro and the flow of fluid altered based on the temperature feedback provided. In an exemplary embodiment, the system 10 may compare temperature and pressure sensed within the kidney to known values and provide a warning when the parameters are outside of a predetermined safe region. The warning may be a visual or audio alert.

In an embodiment, the system 10 may monitor movement of a target structure such as, for example, a kidney stone. The system may calculate the rate of movement based on the original position of the stone and its new position. If the movement exceeds a predetermined threshold, the user may be alerted to manually adjust the flow rate of the system. As described above, flow rate may be adjusted manually via a foot pedal 117, the touch screen interface 112 or a pump interface. In an embodiment, if the system 10 is on auto mode, the system 10 will automatically adjust the flow of irrigation as necessary automatically. This capability may be extremely beneficial during procedures such as a lithotripsy to control retropulsion of the stone.

Figure 9:
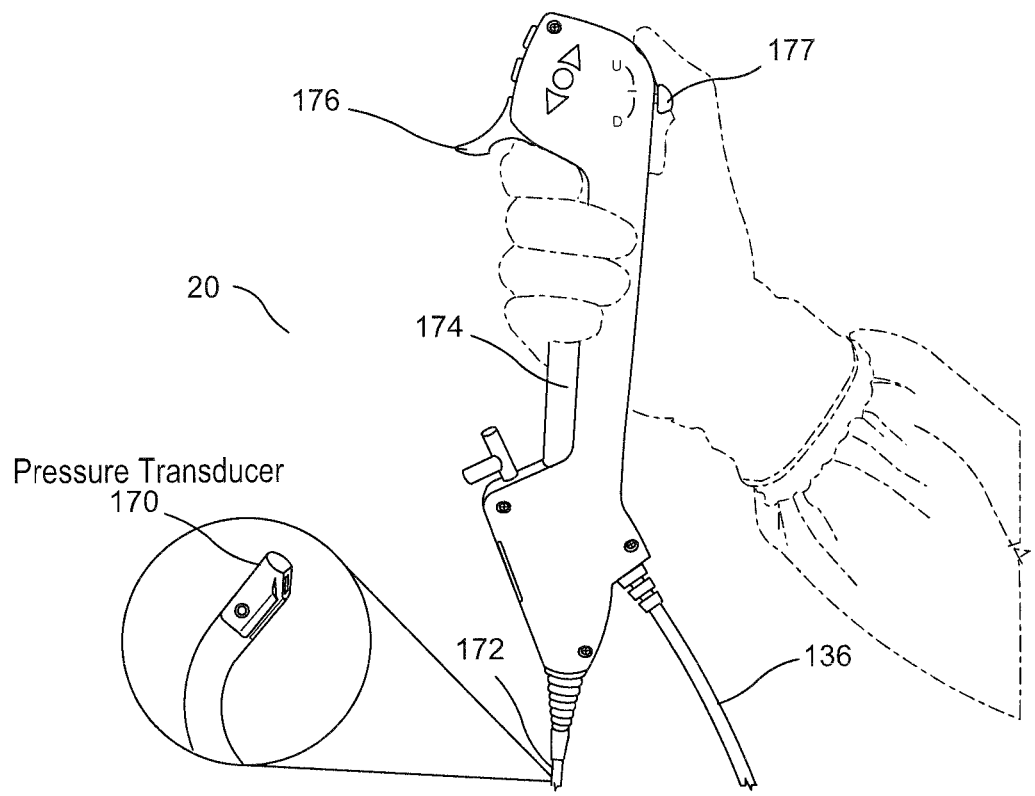
FIG. 9 shows a side view of scope device of the system of FIG. 1 according to an exemplary embodiment.
Figure 10:
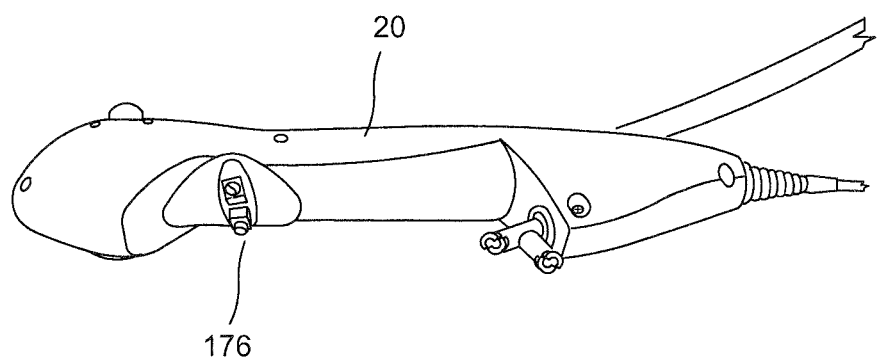
FIG. 10 shows a top view of the scope device of FIG. 9.

The scope device 20, as depicted in FIGS. 9-10, may be, for example, a ureteroscope such as a LithoVue™ scope. The LithoVue™ scope is lighter in weight than many current models, relieving clinician work load. Scope 20 delivers fluid from the fluid management system 10 to the target tissue via a scope shaft 169. The scope 20 is connected to the fluid management system 10 via a supply line (i.e., tube), as described above. The supply lines from the fluid management system 10 to the scope 20 are preferably formed of a material the helps dampen the peristaltic motion created by the pump 126. As shown in FIG. 9, scope 20 may include a pressure transducer 170 at a distal tip of the scope shaft 169 to measure pressure within, for example, the kidney. The scope 20 may also include other sensors such as, for example, a temperature sensor. In an exemplary embodiment, the distal end 172 of the scope 20 may also include at least one camera 128 to provide a visual feed to the user on the display screen 113. In another embodiment, the scope 20 may include two cameras 128 having different communications requirements so that different information may be relayed to the user by each camera 128. In this embodiment, the user may switch back and forth between cameras 128 at will through the touch screen interface 112. The scope 20 includes a handle 174. The handle 174 may have a fluid flow on/off switch 176, which allows the user to control when fluid is flowing through the scope 20 and into the patient. The handle 174 may further include other buttons 177 that perform other various functions. For example, in one embodiment, the scope handle 174 may include buttons to control the temperature of the scope or fluid. In another embodiment, the scope handle 174 may include a laser so that the user may fire laser energy. In an exemplary embodiment, the laser may be a Lumenis or StarMed Tech Laser. A laser fiber may be connected to the laser system and inserted through the ureteroscope working channel. The user may fire the laser so that energy comes out of the laser fiber tip which hits the debris/stone to break it up. In an exemplary embodiment including a laser button on the scope, a communication line between the laser system and the scope is maintained (i.e., hardwire or wireless). It will be understood that while the exemplary embodiment describes a ureteroscope, the features detailed above may also be directly integrated into a cystoscope, hysteroscope, or virtually any device with an image capability. Scope 20 may also include a drainage port 178 which may be connected to a drainage system as described in further detail below.

Figure 6:
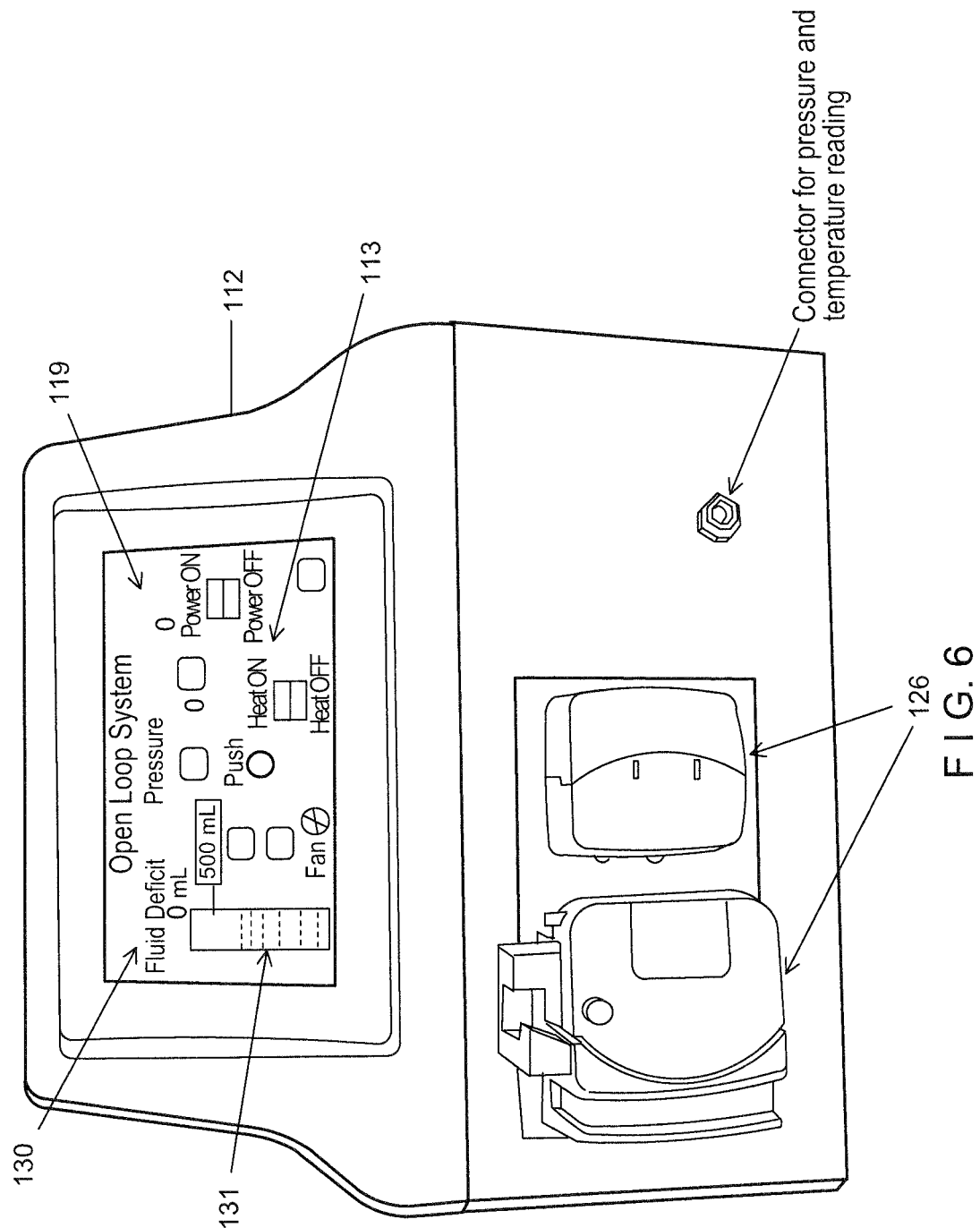
FIG. 6 shows a perspective view of a touch screen interface and pump system of the system of FIG. 1 according to an exemplary embodiment.

The fluid management system 10 may include a fluid deficit monitoring system 130. In an exemplary embodiment, the fluid deficit monitoring system 130 monitors the amount of fluid (i.e., saline) in a fluid bag 104 through weight. In this embodiment, a weight sensor 132 such as a scale is hung from the hook 110. The weight sensor 132 may also include a hook 134 from which one or more fluid bags 104 are suspended. The weight sensor 132 determines a weight of the fluid bag 104 attached to the hanger module 100 to compare an initial amount of fluid in the fluid bag 104 to a current amount of fluid remaining in the fluid bag 104. The readout of the scale is shown to the user on the display screen 113, as illustrated in FIGS. 4-5. As the procedure proceeds, the readout of the scale is updated in real time to alert the physician to how much fluid is left in the fluid bag 104 and this amount may then be used to determine the amount of fluid that has been infused into the patient. In an exemplary embodiment, the system 10 provides the amount of time remaining before a new bag is needed based on the weight of the bag 104 and the rate at which the bag 104 is emptying—i.e., flow rate. In another embodiment, the amount of fluid remaining may be shown as a fluid deficit bar 131, as can be seen in FIG. 6. An alert may be shown on the display screen 113 with an audible signal when, for example, 10% of the saline is left in the bag 104. In an exemplary embodiment, the weight sensor 132 may connect to the display screen 113 via a WiFi signal. In another exemplary embodiment, the weight sensor 132 may be connected to the display screen 113 via a hard wire connection.

In another exemplary embodiment, the fluid deficit monitoring system 130 may include a pressure sensor connected inline between the fluid bag 104 and the device 20. In this embodiment, pressure is determined based on the height of the fluid bag 104. The amount of head pressure decreases as the bag empties. When the pressure falls below a threshold set by the user, an alert is shown on the display screen 113 and an audible signal is emitted. In another exemplary embodiment, the fluid deficit monitoring system 130 may be set to a specific flow rate based on the amount of time that has passed. The physician may enter a bag fluid volume into the system 10 which then calculates the amount of fluid already used and how much is left based on the known flow rate and the amount of time the system 10 has been in use.

The fluid management system 10 may utilize small diameter pump tubing 136 to connect various components. Exemplary tubing 136 for irrigation procedures may be less than or equal to 1/16 inches in diameter. However, it will be understood that tubing size may vary based on the application. Tubing may be disposable and provided sterile and ready to use. Different types of tubing may be used for various functions within the system 10. For example, one type of tubing may be used for fluid heating and fluid flow control to the device 20 while another type of tubing may be used for irrigation within the body.

Figure 11:
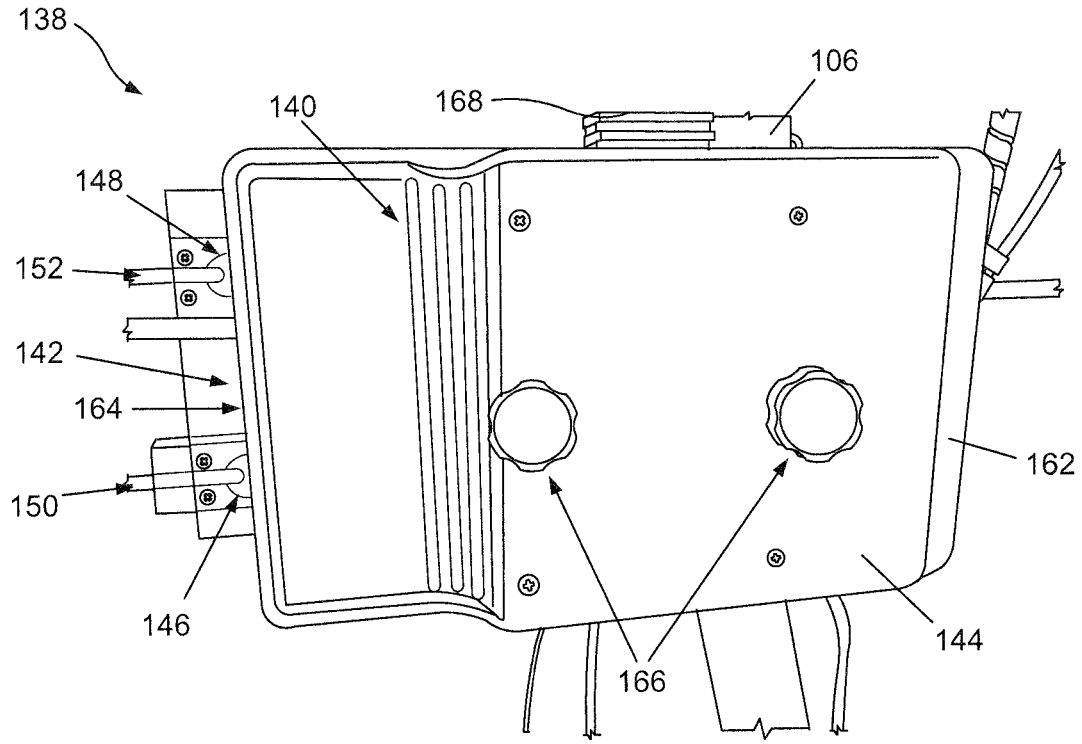
FIG. 11 shows a side view of the heater assembly of the system of FIG. 1 according to an exemplary embodiment.
Figure 12:
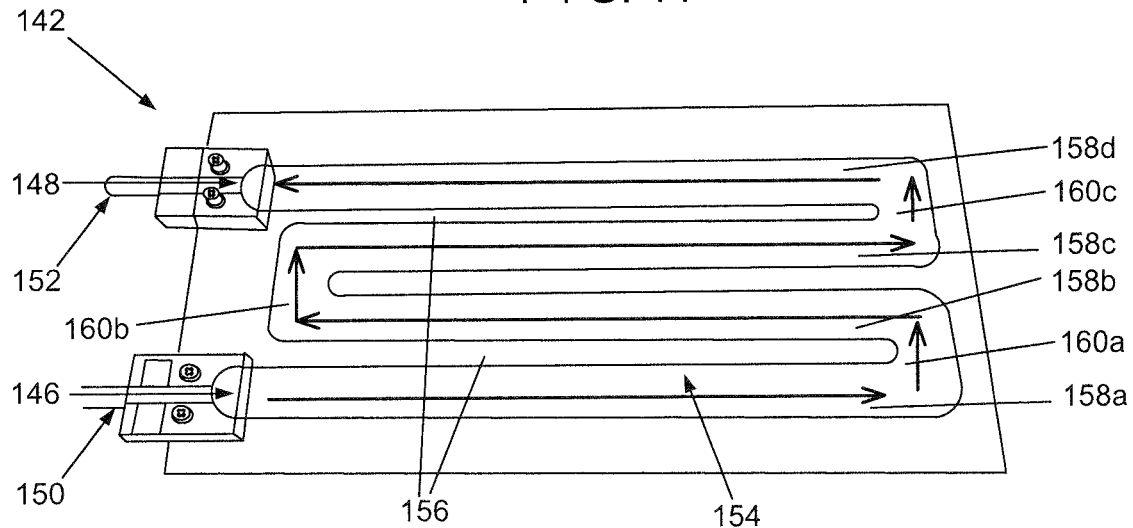
FIG. 12 shows a top view of the heater cassette of the heater assembly of FIG. 11 according to an exemplary embodiment.

In an exemplary embodiment, the fluid management system 10 may optionally include a heater assembly 138 for heating fluid to be delivered to the patient, as shown in FIGS. 11-12. The heater assembly 138 includes a heater 140, a heater cassette 142 and a clamping mechanism 144 for the cassette 142. An exemplary cassette 142 may include a fluid inlet port 146 and a fluid outlet port 148 located at a lateral side of the cassette 142. The fluid inlet and outlet ports 146, 148 each include an inlet and outlet connector 150, 152, respectively, extending from the lateral side of the cassette 142. The connectors 150, 152 may be in the form of luer-lock fittings, barb fittings, quick connect fittings, etc.

The connectors 150, 152 connect the heater assembly 138 to other components of the fluid management system 10. For example, the fluid inlet port 146 may be connected, via a fluid tubing 136 to pump 126 while fluid outlet port 148 is connected to device 20. In an exemplary embodiment, the cassette 142 includes an internal flow path along a channel 154 through which fluid may flow from the inlet connector 150 to the outlet connector 152, as shown in FIG. 12. The cassette 142 may include one fluid path or multiple fluid paths. If multiple fluid paths exist, one or more walls 156 may separate the various fluid channels 154. The exemplary fluid channel 154 includes horizontal sections 158 and vertical sections 160 to form a convoluted fluid path between the fluid inlet port 146 and the fluid outlet port 148. The fluid channel 154 is configured to provide a substantial amount of outwardly facing surface area relative to the internal volume to promote efficient warming of the fluids by the heater 140. In an exemplary embodiment, fluid enters the cassette 142 via the inlet port 146 and into lower horizontal section 158a. Fluid flows through the vertical section 160a and reverses direction to flow through the first middle horizontal section 158b. The fluid follows the channel 154 in this manner until it flows through the outlet port 148. The sections 158, 160 of the channel 154 are separated by horizontal walls 156. The cassette 142 may be formed of, for example, polycarbonate or any high heat rated biocompatible plastic and is formed as a single piece or a plurality of pieces permanently bonded to one another. The inlet and outlet connectors 150, 152 may be integrally formed with the cassette 142 or may be separately installed pieces as would be understood by those skilled in the art.

The cassette 142 is coupled to the heater 140 via the clamping mechanism 144. In the exemplary embodiment of FIG. 11, the clamping mechanism 144 is configured as two side plates 162 with a slot 164 extending between the side plates 162 for receiving the cassette 142. In an exemplary embodiment, the slot 164 may include a guide (not shown) to assist the user in inserting the cassette 142 into the slot 164. When inserted into the slot 164, the side plates 162 are clamped about the cassette 142 via two knobs 166. Rotation of the knobs 166 in a first direction moves the side plates 162 closer together to clamp the cassette 142 in place between them while rotation of the knobs 166 in a second direction moves the side plates 162 apart to allow the cassette 142 to be slid from the slot 164. The clamping mechanism 144 may be attached to the pole 106 by any means such as, for example, adjustable pole clamps so that the clamping mechanism 144 and the heater assembly 138 may be slid along the pole 106 to a desired location.

The cassette 142 is designed so that the channel sections 158, 160 are substantially aligned with the heater 140 when the cassette 142 has been inserted into a slot 164 of the heater assembly 138, as illustrated in FIG. 11. The heater 140 may include one or more heat sources such as, for example a platen system or an in line coil in the fluid supply line using electrical energy. Heating may be specifically designed and tailored to the flow rates required in the specific application of the system 10. The heater 140 may be located in one or both of the side plates 162. In an exemplary embodiment, the heater 140 encompasses the entire inner surface area of the plates 162. In another exemplary embodiment, the heater 140 may be located only at an upper portion of one or both of the plates 162. It will be understood that the heater 140 may be located anywhere in the heater assembly 138 adjacent to the fluid flowing therethrough.

The heater assembly 138 may include a heater user interface 168. The heater user interface 168 may simply be a display screen (not shown) may providing a digital display of the internal temperature of the heater. In another embodiment, the user interface 168 may also include temperature adjustment buttons to increase or decrease the temperature of the heater 140. In this embodiment, the heater display screen (not shown) may indicate the current temperature of the heater as well as the target temperature to be reached. It is noted that all information output from the heater assembly 138 may be transmitted directly to the display screen 113 such that no heater user interface 168 is necessary.

In an exemplary embodiment, temperature sensors are mounted in the heater assembly 140 such that they detect the temperature of the fluid flowing through the cassette 142. Sensors may be located at or near the fluid inlet port 146 and the fluid outlet port 148. In an exemplary embodiment, temperature sensors may be mounted so that they detect the temperature of fluid flowing through the cassette 142 prior to the fluid entering the channel 154 and after fluid exits the fluid channel 154. In some embodiments, additional sensors may be located at a medial portion of the channel 154 so that they detect the progression of temperature increase of the fluid in the cassette 142. Sensors may remotely send any information to the display screen 113 or they may send information to heater user interface display screen. In another embodiment, sensors are hardwired with the heater user interface 168 which is then able to remotely transmit desired information to the system display screen 113.

Figure 13:
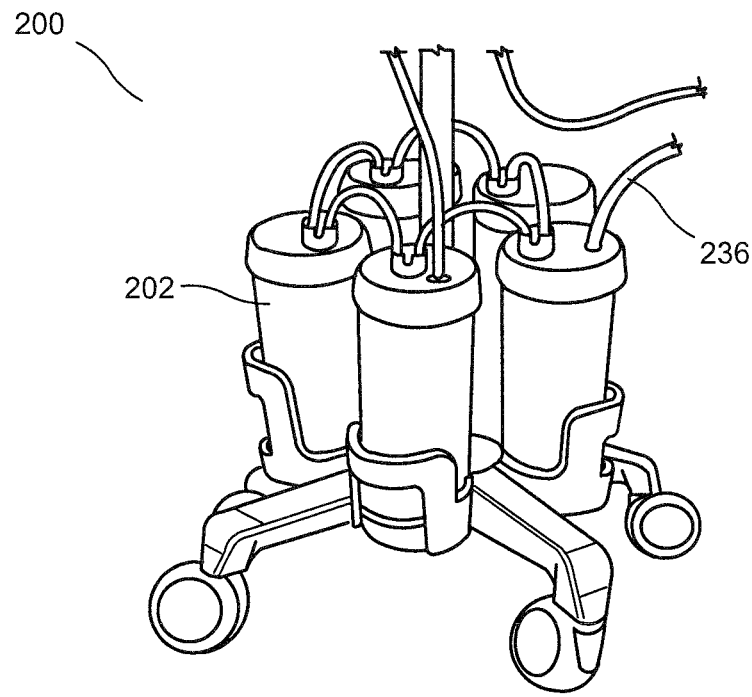
FIG. 13 shows a perspective view of a waste management system of the system of FIG. 1 according to an exemplary embodiment.
Figure 34:
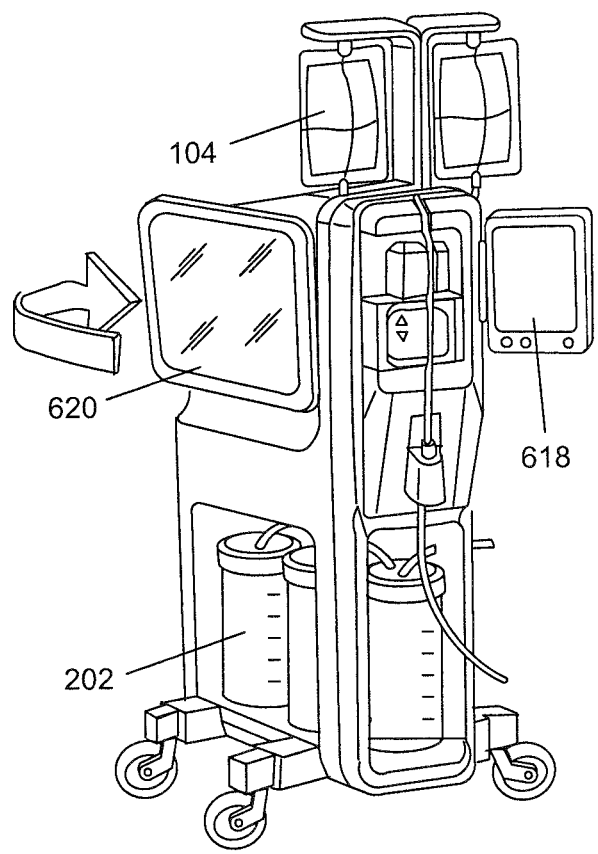
FIG. 34 shows a perspective view of a waste management system configuration according to a tenth exemplary embodiment.

The fluid management system 10 may include a waste management system 200. An exemplary waste management system may simply be tubing leading from a fluid disposal port in the scope 20 to a drainage bag or collection vessel 180. Collection of waste can be via canisters on a platform or a direct feed to an alternate system. In an embodiment shown in FIG. 13, for example, one or more waste collection vessels, or canisters 202 (five in this embodiment), may be used in combination with a vacuum pump (not shown) to draw waste from the patient to the collection vessels 202. It will be understood that while the embodiments herein show five collection vessels, any number of vessels may be used. For example, FIG. 34 depicts another exemplary embodiment using three collection vessels. Tubing 236 linearly connects each of the collection vessels 202 to one another so that the collection vessels 202 are filled one at a time. Specifically, when the first collection vessel 202 is full, the waste starts to flow into the subsequent collection vessel, and so forth, until each of the collection vessels is full. However, one concern with this "daisy chain" system is that the vacuum (not shown) must be shut down to swap the filled waste collection vessels 202 out of the system. Furthermore, the system 200 is not easily pre-plumbed to install or remove as a set when full, increasing potential vacuum down time.

Figure 14:
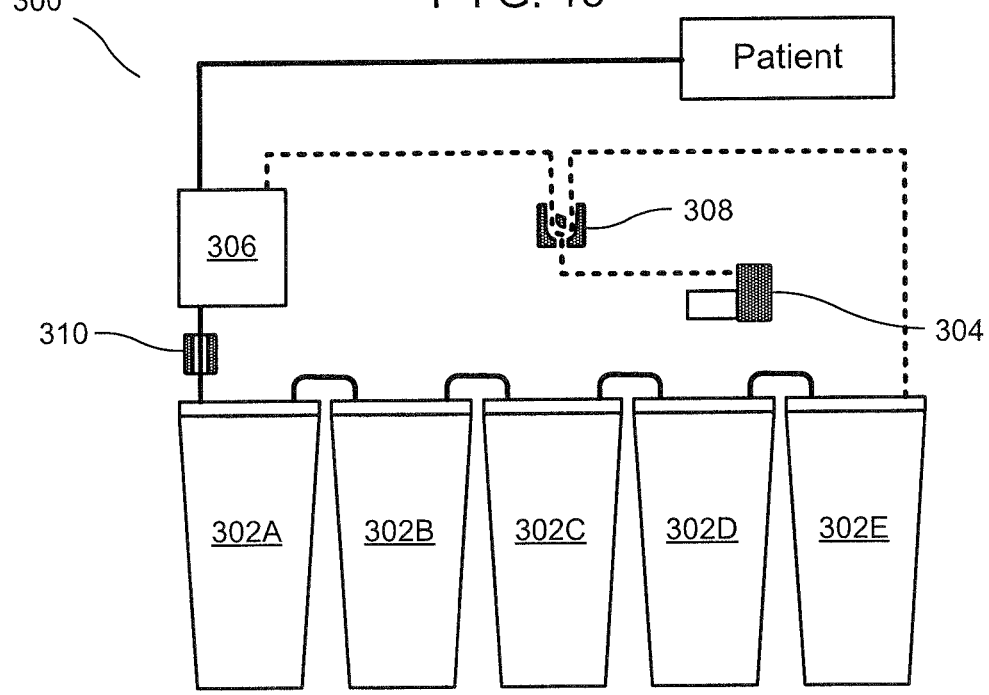
FIG. 14 shows a schematic view of a waste management system of the system of FIG. 1 according to a second exemplary embodiment.

In FIG. 14, a waste management system 300 according to an alternate embodiment is shown, which address the concerns of the "daisy chain" system. In this embodiment, similar to the waste management system 200, five collection vessels 302A-E and a vacuum pump 304 are used. However, it will be understood that any number of collection vessels may be used, depending on the procedure. In this embodiment, an intermediate holding chamber 306, a dual-position valve 308, and a traditional pinch valve 310 are also included in the system. The intermediate holding chamber 306 is connected to the patient, the first collection vessel 302A and the dual-position pinch valve 310. The pinch valve 310 is positioned between the intermediate holding chamber 306 and the first collection vessel 302A and can be operated to permit or prevent flow of fluid waste into the first collection vessel 302A. The first collection vessel 302A is connected to the second vessel 302B, which is connected to the third vessel 302C, and so forth. The vacuum pump 304 is connected to both the intermediate holding chamber 306 and the last collection vessel 302E via tubing 336 and the dual-position pinch valve 308, which is a Y-pinch valve, as shown in FIG. 14. The dual position pinch valve 308 may be activated to allow flow to either the waste collection vessels 302A-E or the intermediate holding chamber 306.

In use, waste fluid is pumped from the patient through the intermediate holding chamber 306 and into the waste collection vessels 302. When the waste collection vessels 302 are full, the pinch valve 310 and the dual-position valve 308 are activated so that the connection between the patient and the waste collection vessels 302 is blocked, preventing flow of waste into the collection vessels 302 permitting a user to substitute empty vessels for the full vessels or to empty and replace the full vessels. When this occurs, the intermediate holding chamber 306 collects waste from the patient until the pinch valves 308, 310 are switched back to allow flow to the collection vessels 302 again. Thus, the system 300 allows a user to easily switch out used collection vessels 302 without having to shut down the vacuum 304 or stop the flow of waste from the patient.

Figure 15:
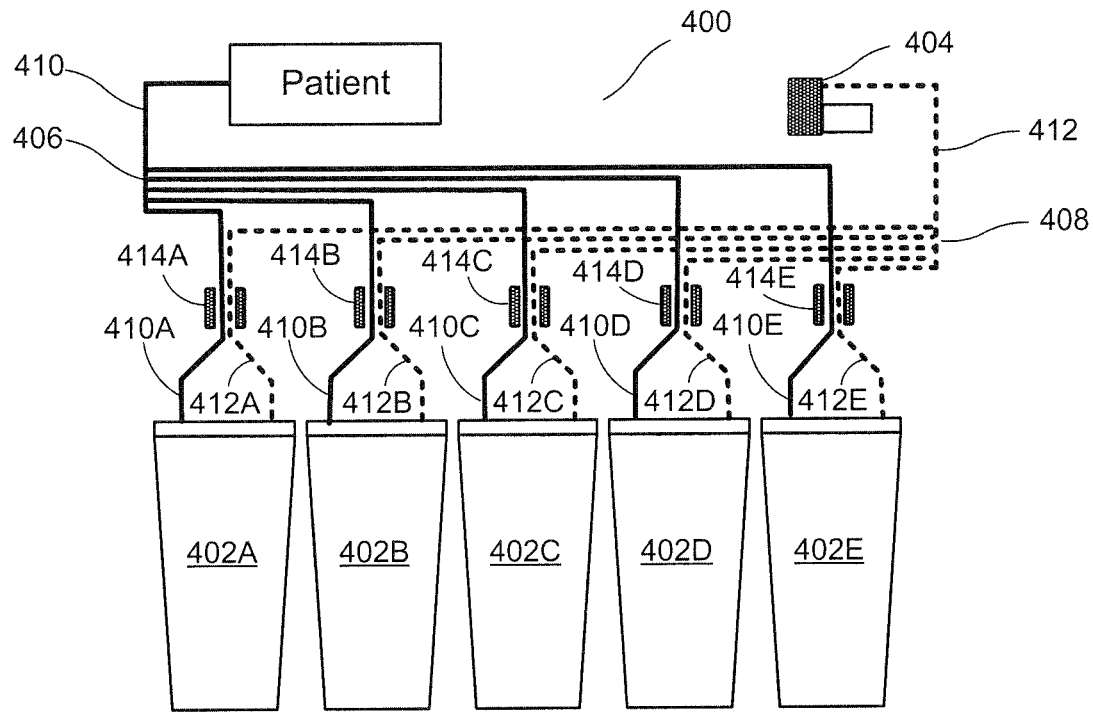
FIG. 15 shows a schematic view of a waste management system of the system of FIG. 1 according to a third exemplary embodiment.

In an exemplary embodiment, according to FIG. 15, a two manifold waste management system 400 is shown. In this embodiment, the waste management system uses one manifold 406 for waste and another manifold 408 for the vacuum pump 404. Specifically, one tubing line 410 extends from the patient and branches into individual tubes 410A-E with each of the tubes 410A-E extending to a corresponding one of the collection vessels 402. A second tubing line 412 extends from the vacuum pump 404 and similarly branches into individual tubes 412A-E each of which extends to a corresponding one of the collection vessels 402A-E. Thus, both the patient and the vacuum 404 are individually and separately connected to each of the collection vessels 402A-E. A plurality of pinch valve 414A-E a provided with each being positioned on a corresponding one of the tubing lines 410A-E, 412A-E to control waste flow and vacuum suction to the corresponding collection vessel 402A-E, as shown in FIG. 15. In use, the pinch valves 414A-E may be activated to shut off both the vacuum pump 404 and stop waste flow to unused collection vessels, controlling flow to enter only one collection vessel at a time. Also, when a collection vessel 402 is full, the corresponding pinch valve 414 may be activated, shutting off both vacuum and waste flow to the full collection vessel and allowing removal of the full collection vessel without interfering with the flow of waste to other collection vessels with free space.

Figure 16:
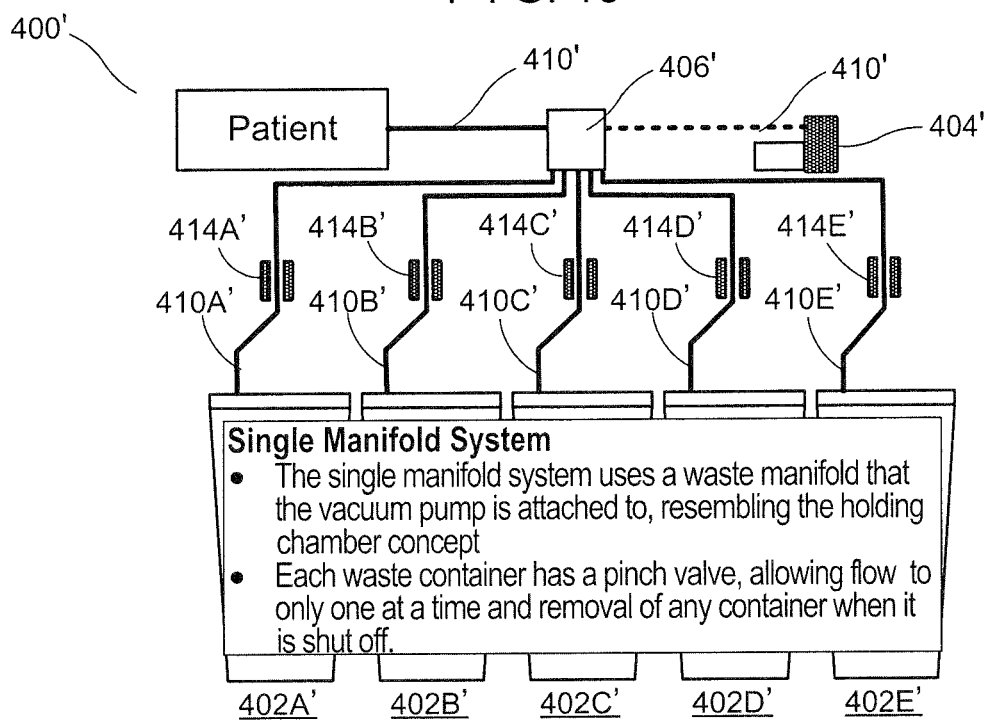
FIG. 16 shows a schematic view of a waste management system of the system of FIG. 1 according to a fourth exemplary embodiment.

FIG. 16 shows an exemplary embodiment with a single manifold waste management system 402'. In this embodiment, the waste management system uses a single tubing manifold 406' that attaches both the patient and the vacuum pump to each of the individual collection vessels. Specifically, two tubing lines 410' extending from the patient and vacuum pump 404' branch into individual tubes 410A-E' each of which extends a corresponding one of the collection vessels 402'. Similarly to the system 400, each collection vessel 402A-E' has an associated pinch valve 414A-E' which controls flow to the corresponding collection vessel so that, for example, flow may be permitted to only a single collection vessel at a time. Thus, the pinch valves may be operated to permit or prevent flow to the collection vessels in any desired combination, enabling the removal of full collection vessels without interfering with the flow of waste to other collection vessels that have remaining space.

Figure 17:
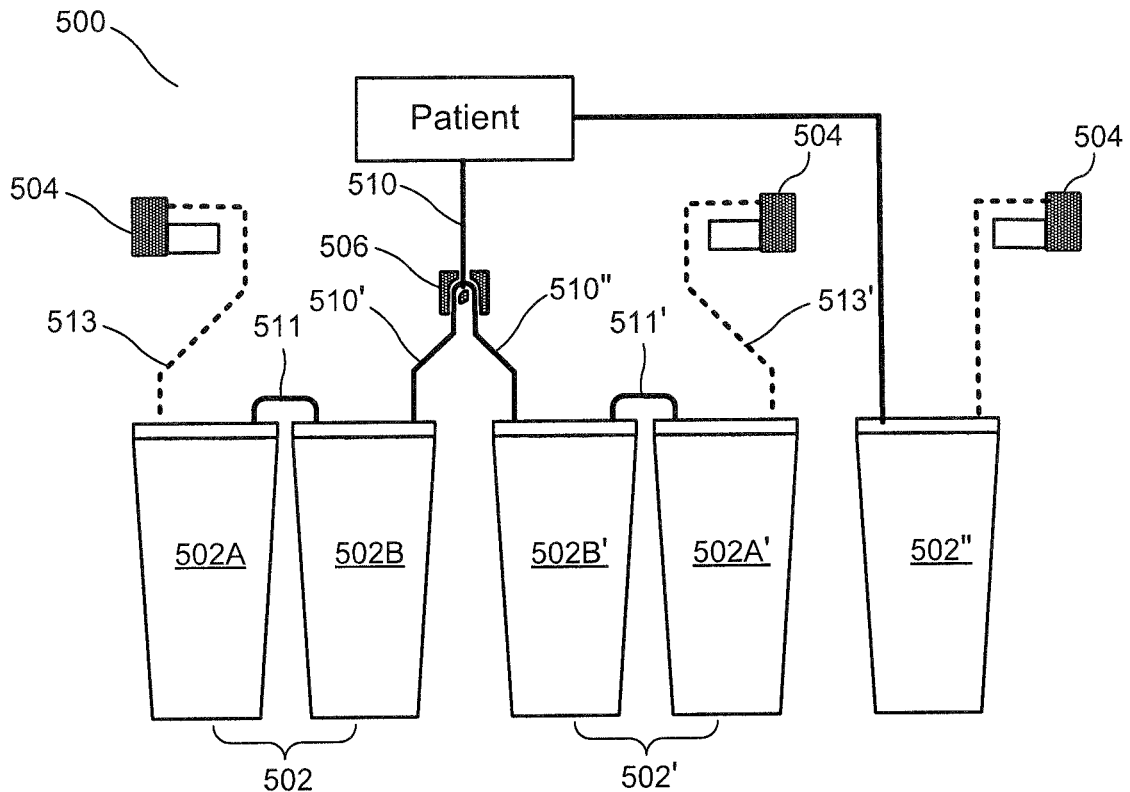
FIG. 17 shows a schematic view of a waste management system of the system of FIG. 1 according to a fifth exemplary embodiment.
Figure 18:
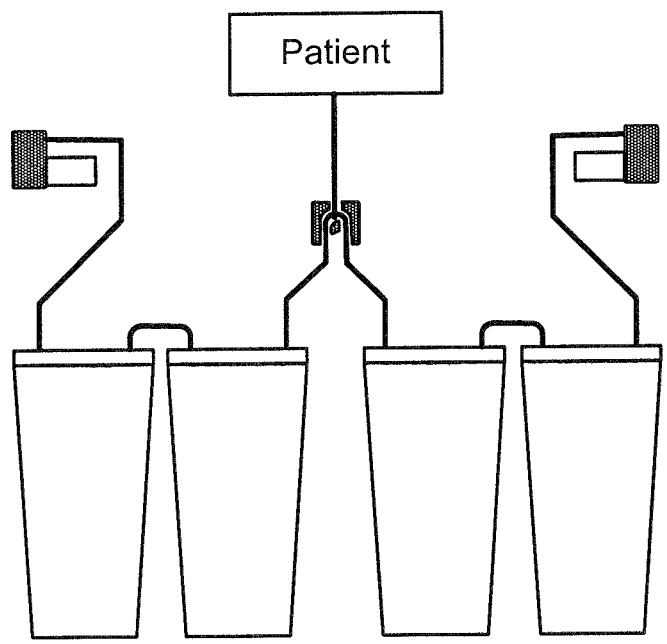
FIG. 18 shows a schematic view of a waste management system of the system of FIG. 1 according to a sixth exemplary embodiment.

In another exemplary embodiment, according to FIG. 17, a waste management system 500 includes three vacuum pumps 504 and a dual-position pinch valve 506. In this embodiment, each set 502, 502' of two collection vessels (502A and B in set 502 and 502A', 502B' in set 502') has its own vacuum pump 504. A separate collection vessel 502" includes a pump 504 for a drape. A tubing line 510 extends from the patient, and branches at the pinch valve 506 into separate tubes 510', 510" each extending to a corresponding one of the sets of collection vessels 502, 502'. That is, a first collection vessel 502B, 502B' of each of the sets of collection vessels 502 is connected to the patient via the tubes 510' and 510", respectively, while the second collection vessels 502A, 502A' of each set 502 are connected to the first collection vessel 502A, 502A' via the connecting tubes 511 and 511', respectively, and are connected to the vacuum pumps 514 via tubes 513, 513', respectively. The dual-position pinch valve 506 is positioned between the patient and the sets of collection vessels 502 and is operated to permit the flow of waste into only one collection vessel at a time. This limitation of the flow of waste enables a full waste collection vessel to be changed or emptied as needed while flow continues to the other vessel. In another exemplary embodiment shown in FIG. 18, the system may be used as a two-vacuum system without a drape vacuum.

Figure 19:
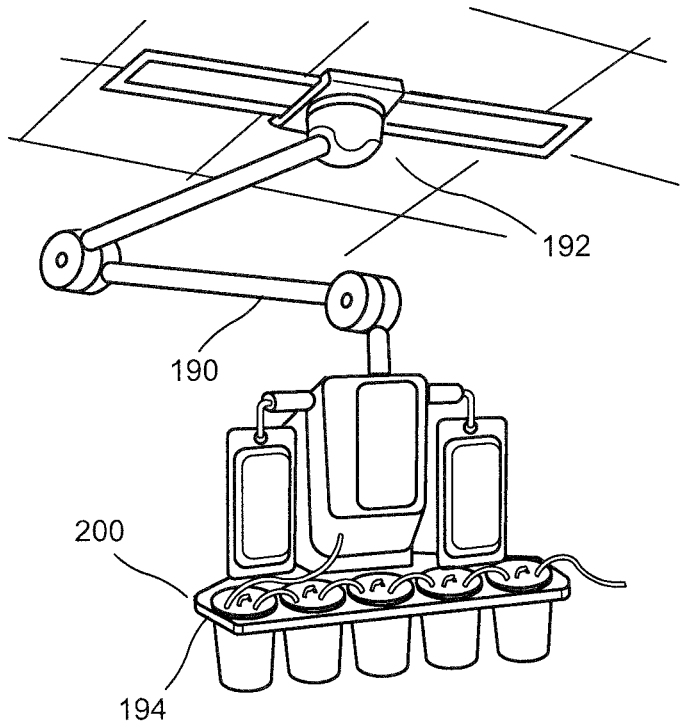
FIG. 19 shows a perspective view of a waste management system ceiling mount according to an exemplary embodiment.
Figure 20:
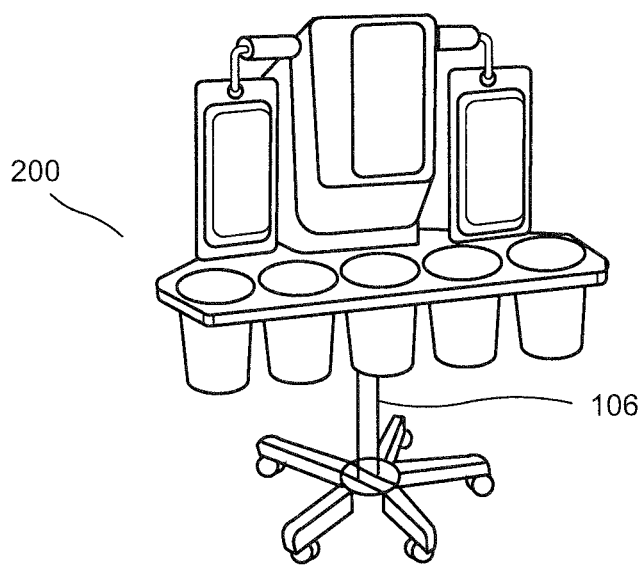
FIG. 20 shows a perspective view of a waste management system mount according to another exemplary embodiment.
Figure 21:
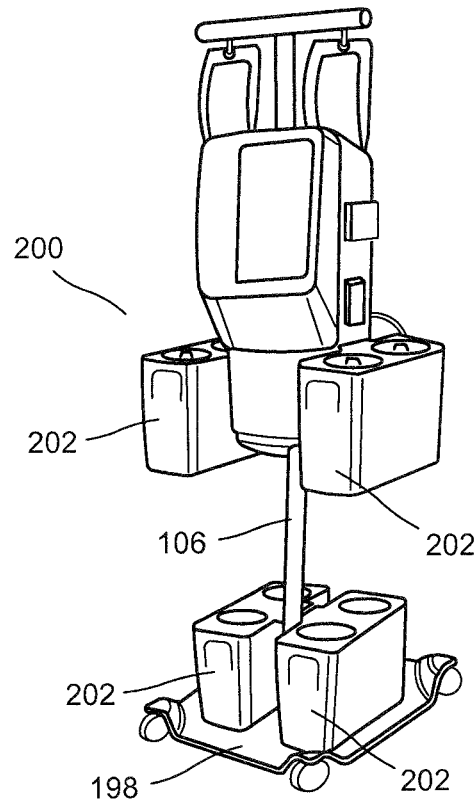
FIG. 21 shows a perspective view of a waste management system mount according to another exemplary embodiment.
Figure 22:
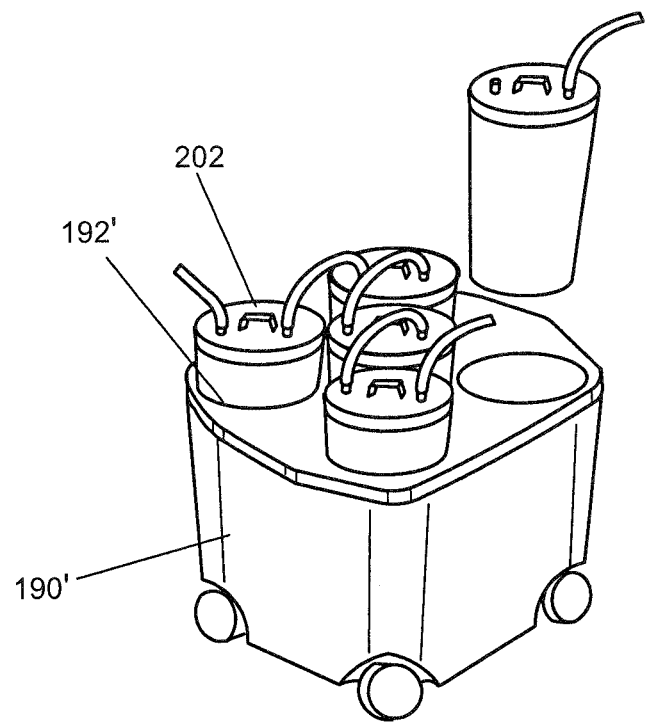
FIG. 22 shows a perspective view of a waste collection module according to an exemplary embodiment of the present disclosure.
Figure 23:
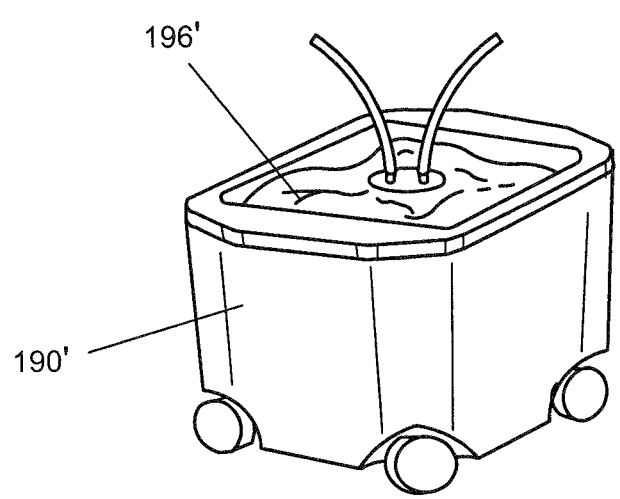
FIG. 23 shows a perspective view of a waste collection module according to another exemplary embodiment of the present disclosure.

In use, the components of the waste management systems 200-500 may be arranged in various configurations depending on the procedure to promote accessibility and functionality. In a first embodiment, shown in FIG. 19, the waste management system 200 may be mounted to a ceiling 192. It will be understood that any of the waste management systems 300, 400, 400' and 500 may be arranged using the various configurations described herein. In this embodiment, waste collection vessels 202 may be nested in a front shelf 194 and be in-line with one another for ease of access and removal. This ceiling mount assembly 190 keeps clutter off the floor in procedures where space is limited. In another exemplary embodiment shown in FIG. 20, which is further discussed below, the waste management system 200 may include a universal mount (not shown) to facilitate mounting to, for example, an IV pole. It will be understood that the universal mount may also be used to mount the waste management system 200 to a wall mount, or even a tabletop configuration. In another exemplary embodiment, in-use waste collection vessels may be attached to an IV pole 106 at waist height to allow for easier removal and disposal, as can be seen in FIG. 21. In this embodiment, two or four waste collection vessels 202 are held in each waist-level assembly 196, while on-deck (not in use) waste collection vessels 202 are position on a lower storage platform 198. In another exemplary embodiment, shown in FIG. 22, the waste management system may include a separate module for the waste collection vessels 202, such as a floor caddy 190'. In this embodiment, the floor caddy 190' may include individual compartments 192' for each of the waste collection vessels 202. However, it will be understood that the floor caddy 190' may instead include a single compartment to hold all of the waste collection vessels or a single disposable waste bag 196', as shown in FIG. 23. The floor caddy 190' may include wheels so that the collection vessels may be rolled around as necessary to stay out of the way in the surgical suite.

In order to optimize ergonomics, accessibility and functionality of the fluid management system 10, the major subsystems, components and modules of the fluid management system 10 may be arranged in various configurations depending on the procedure. For example, the location of the pumps, saline bags, touch screen, etc. can be arranged to any configuration desired to optimize access by a surgeon or those assisting in a surgery depending on the procedure to be performed. In exemplary embodiments, shown in FIGS. 24-34, the fluid management system 10 is configured as a vertical stack of major components and modular options on a vertical IV pole 106 with a rolling base 108. This vertical stacking of the components decreases the width of the fluid management system 10 (i.e., the fluid management system 10 is narrower), making the system 10 more compact so that it can be situated in confined areas within, for example, an operating room. In these embodiments, the pole 106 may include a bend 602 at a lower portion thereof so that each of the components and modular options may be coupled to the front of the pole 106 without disturbing the weight distribution of the system 10.

Figure 24:
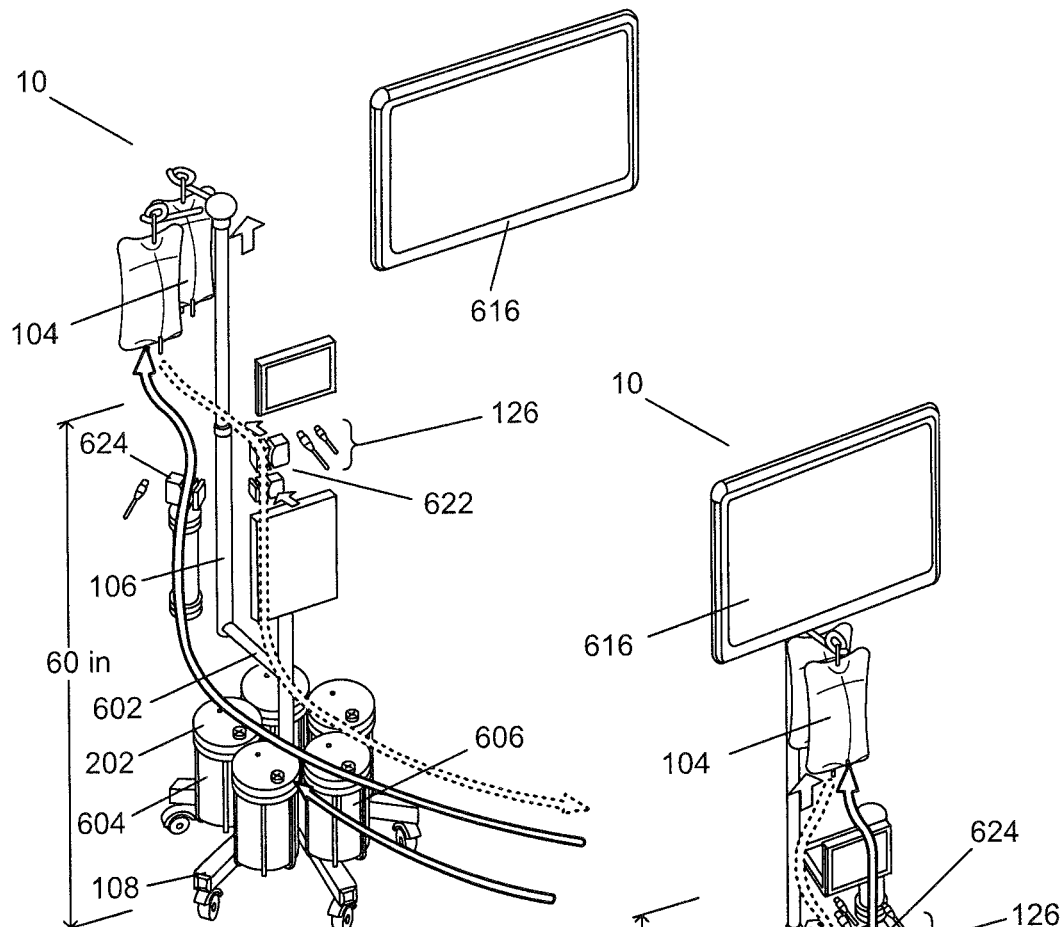
FIG. 24 shows a perspective view of a waste management system configuration according to an exemplary embodiment of the present disclosure.
Figure 26:
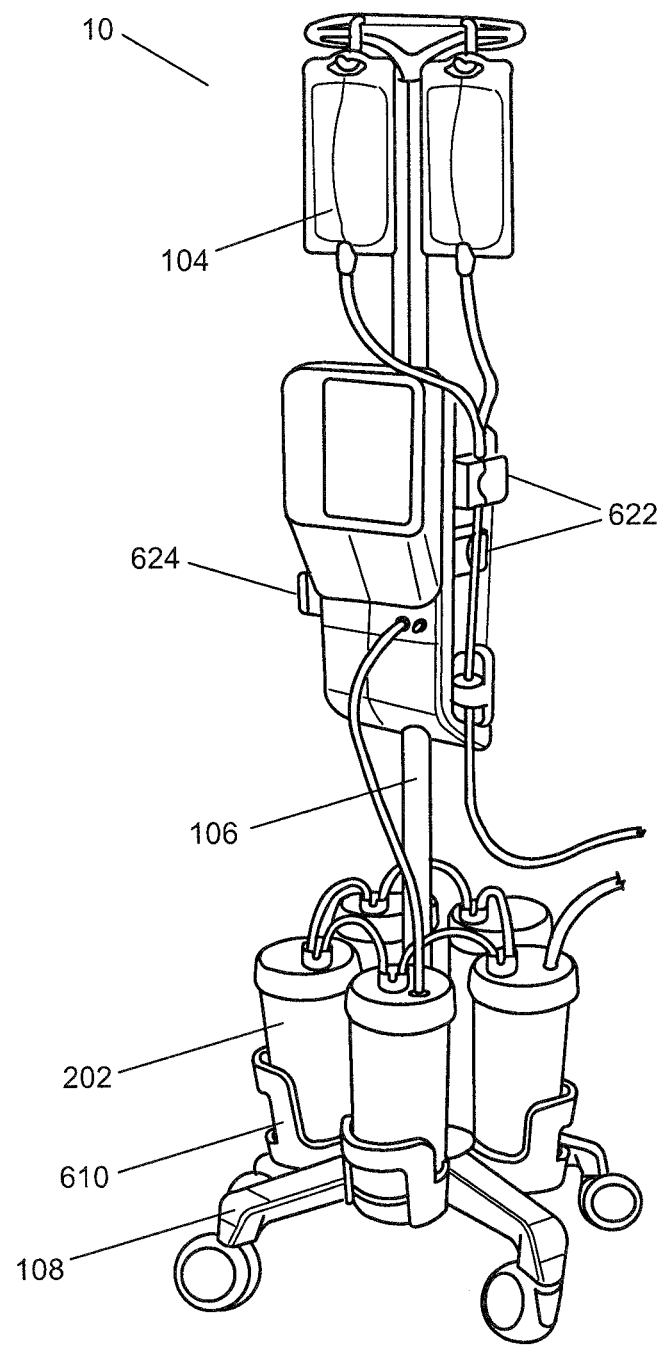
FIG. 26 shows a perspective view of a waste management system configuration according to a third exemplary embodiment.
Figure 27:
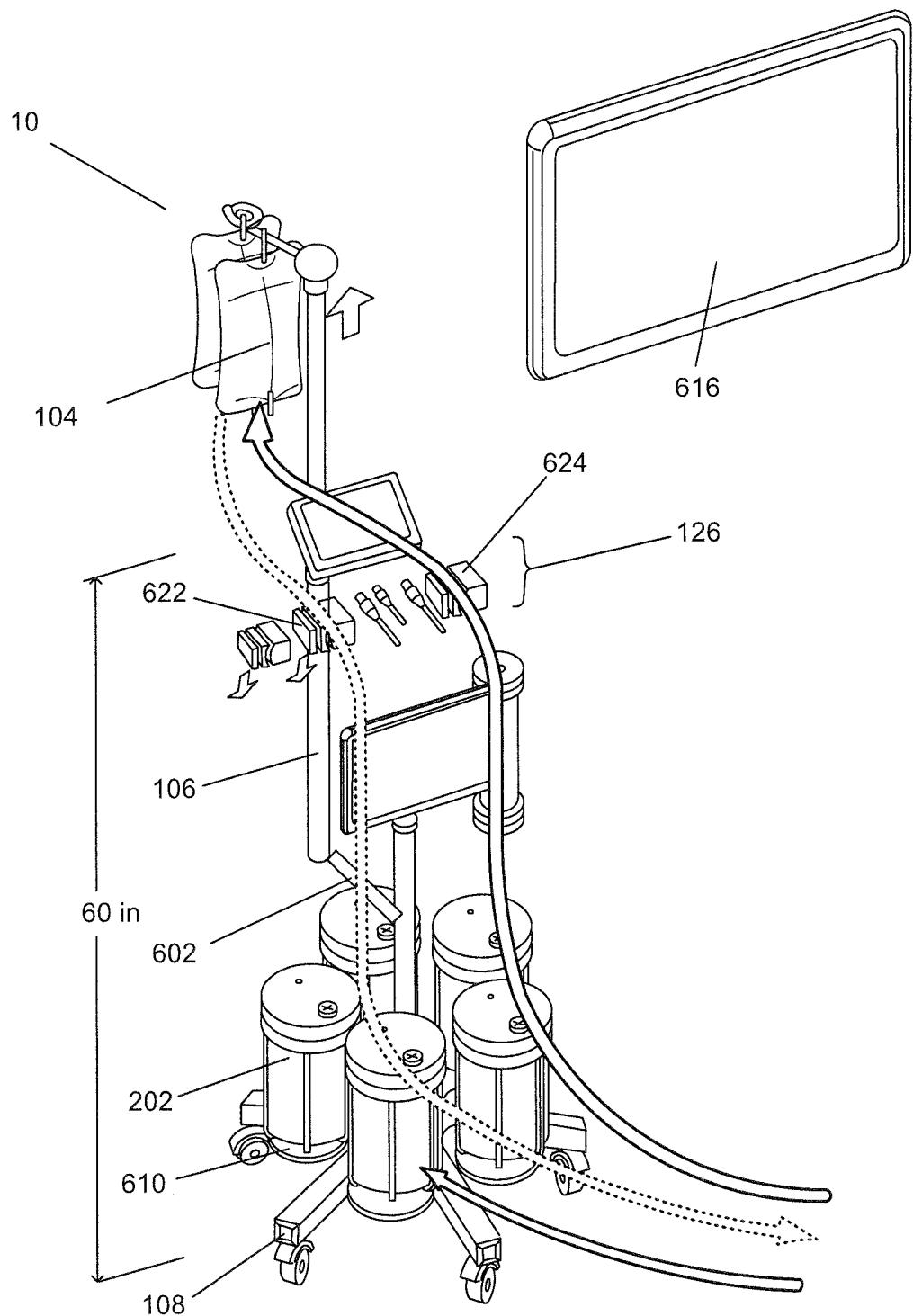
FIG. 27 shows a perspective view of a waste management system configuration according to a fourth exemplary embodiment.
Figure 28:
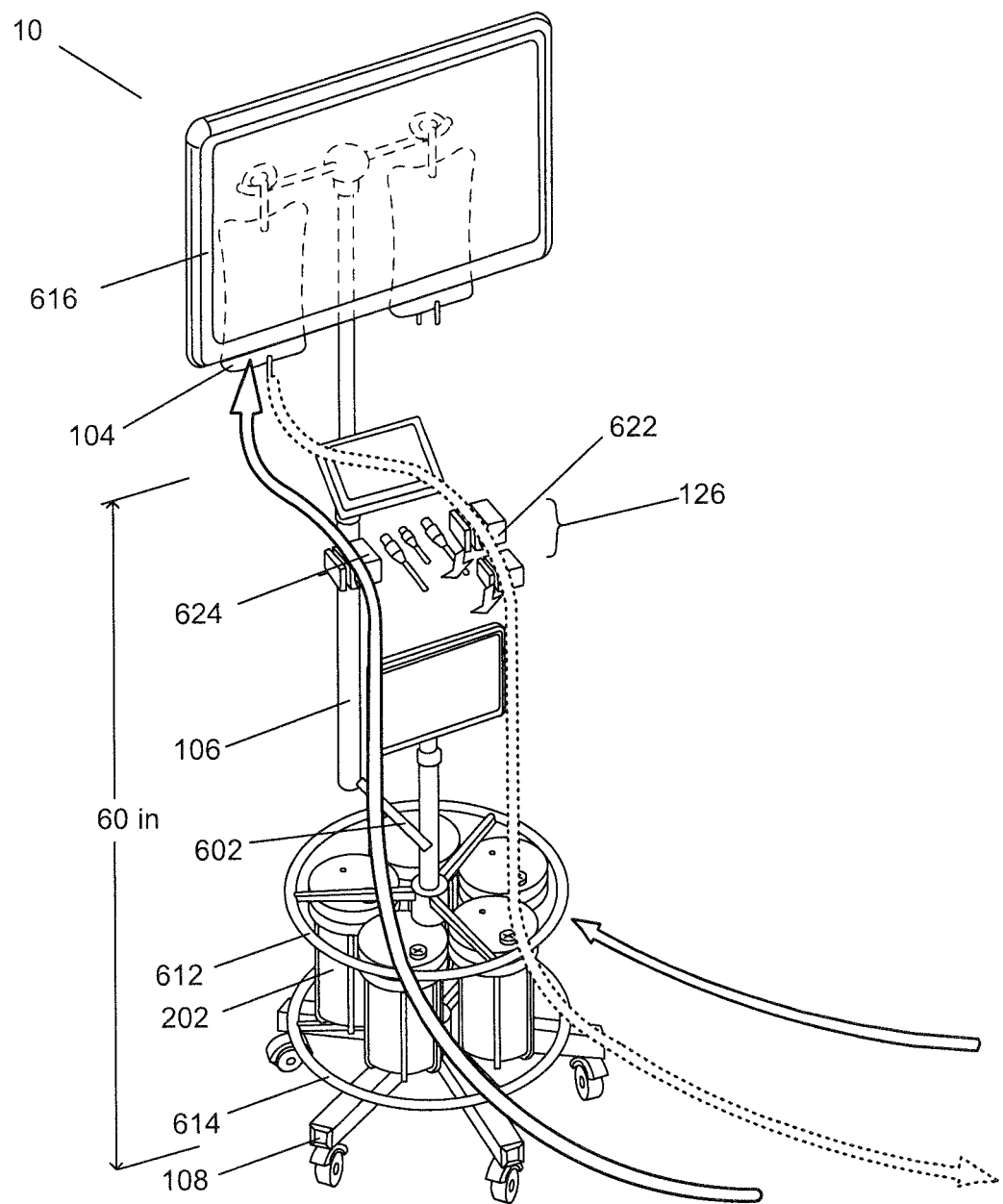
FIG. 28 shows a perspective view of a waste management system configuration according to a fourth exemplary embodiment.
Figure 29:
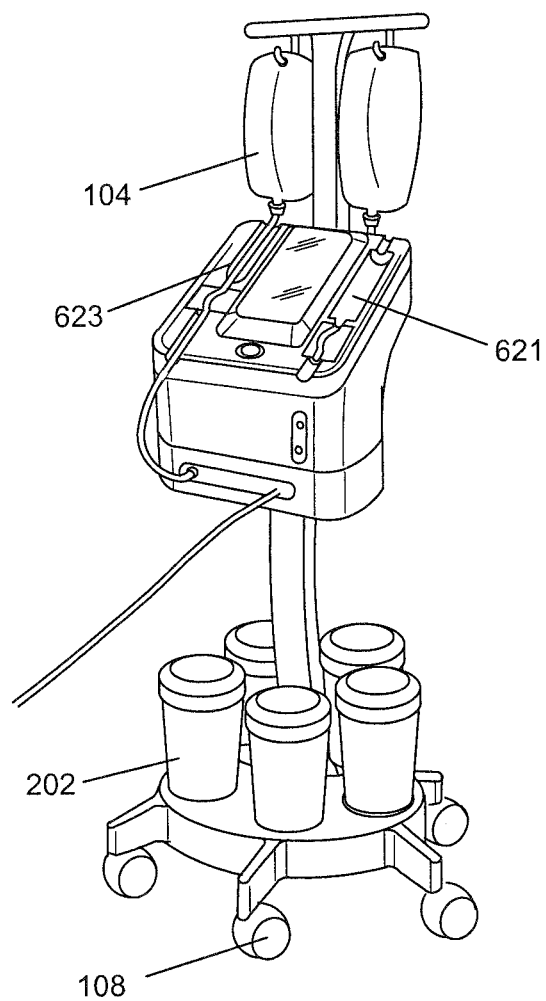
FIG. 29 shows a perspective view of a waste management system configuration according to a fifth exemplary embodiment.

The collection vessels 202, in this embodiment, are positioned around the bottom of the pole 106 in a compact configuration. In an exemplary embodiment, shown in FIG. 24, the collection vessels are weighed by a hanging weight mechanism 604. The hanging weight mechanism 604 may be coupled to the pole 106 and include multiple individual compartments 606 for loading the collection vessels 202. In the embodiments of FIGS. 24 and 26, the hanging weight mechanism 604 includes five compartments 606. However, it is understood that any number of collection vessel compartments 606 may be used depending on the procedure and fluid waste levels. The compartments 606 each include a hole (not shown) into which the collection vessel 202 is placed. The hanging weight mechanism 604 may include a weight sensor (not shown). In another embodiment, the individual compartment 604 may include a weight sensor (not shown) for detecting the changes in weight of the vessel 202 loaded in the respective compartment. In other embodiments, shown in FIGS. 26-27, the collection vessels 202 may be loaded onto individual base plates 610. The base plates 610 may each include a weight sensor (not shown), which detects the changes in weight of the collection vessel 202 loaded on the respective base plate 610. In another exemplary embodiment, the collection vessels may be loaded into a revolving cartridge 612, as shown in FIG. 28. This cartridge 612 may be revolved manually or automatically. Additional support 614 may be added to stabilize the cartridge 612 and the collection vessels 202. In this embodiment, the collection vessels may be weighed as a group or individually. Alternatively, changes in levels of fluid within the collection vessels may be monitored using an optical level sensor (not shown).

Figure 25:
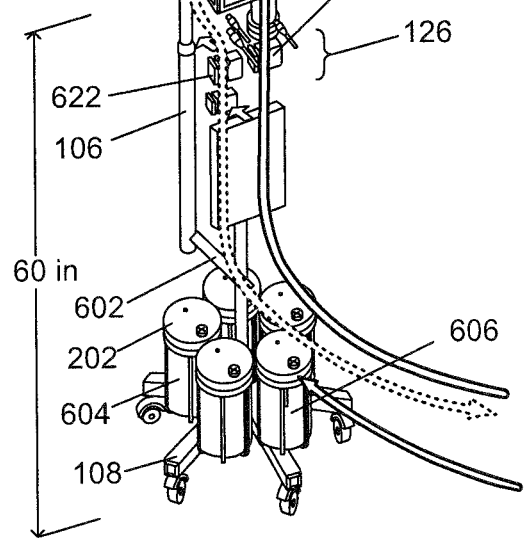
FIG. 25 shows a perspective view of a waste management system configuration according to another exemplary embodiment.
Figure 31:
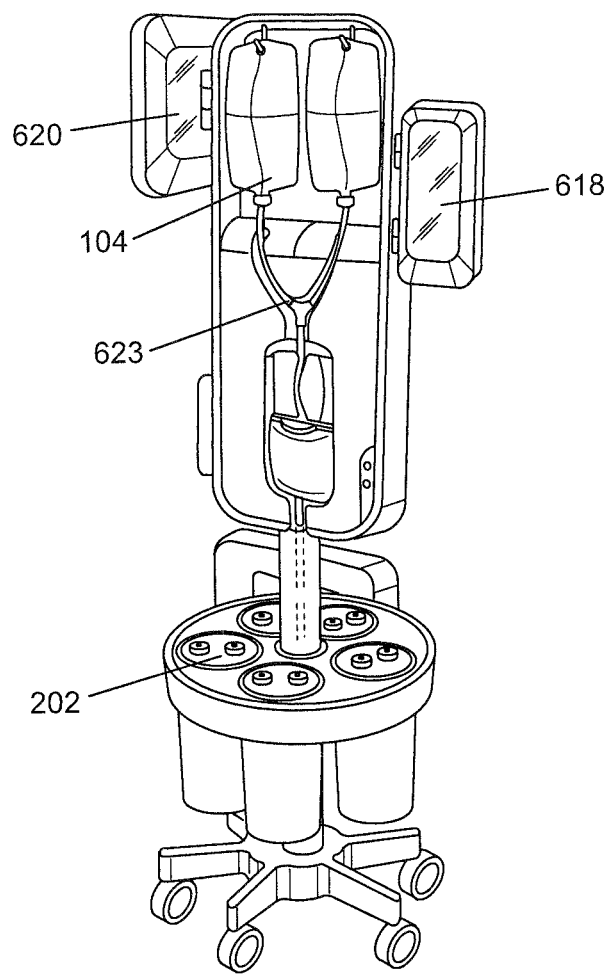
FIG. 31 shows a perspective view of a waste management system configuration according to a seventh exemplary embodiment.
Figure 32:
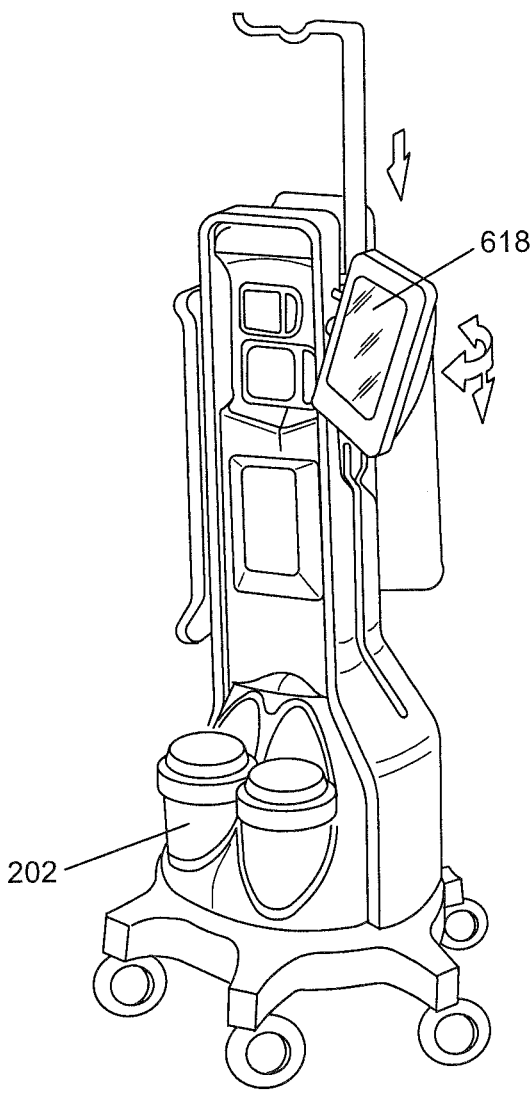
FIG. 32 shows a perspective view of a waste management system configuration according to an eighth exemplary embodiment.
Figure 33:
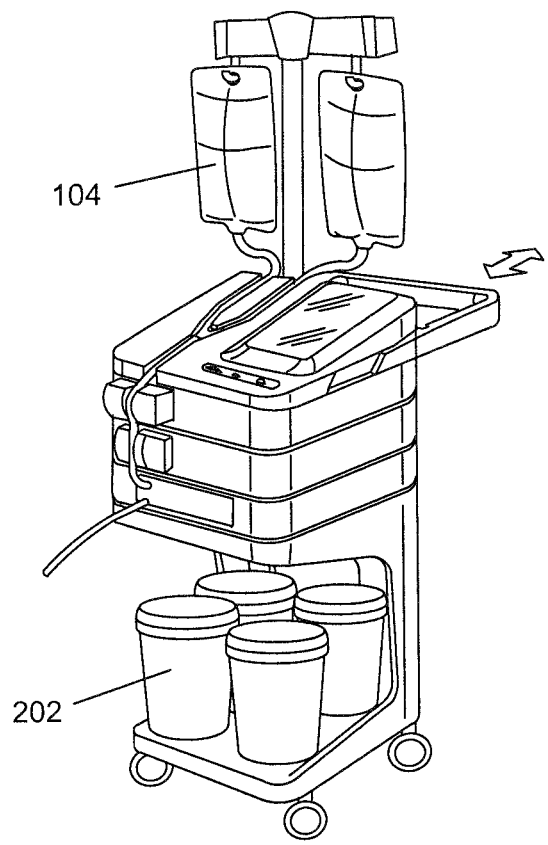
FIG. 33 shows a perspective view of a waste management system configuration according to a ninth exemplary embodiment.

Depending on the preferences of the user or the limitations of available space, a display unit 616 may or may not be integrated with the vertical stack of components. For example, it may be preferable to have the display unit 616 positioned on a table at a different viewing angle from any that can be provided if the display were coupled to the pole 106. Or, in another example, integrating the display unit 616 with the stacked components may increase the height of the vertical stack so that it would not fit within a designated space in the surgical suite. In these cases, such as the embodiments depicted in FIGS. 24 and 27, the display unit 616 is not integrated with the IV pole and stacked components, but is a separate display unit to be placed where desired. In other embodiments, however, the display unit 616 may be coupled to, for example, the top of the bent IV pole 106, as can be seen in FIGS. 25, 28. This position of the display unit 616 at the top of the IV pole 106 allows for greater visibility by the users while preventing the display unit 161 from being blocked by other components of the system 10. In some embodiments, multiple display screens may be used for a multi-imaging modality. For example, in embodiments shown in FIGS. 31 and 34, the system 10 may include an operator display 618 and a surgical display 620. In this embodiment, the display screens 618, 620 may be positioned to promote visibility within the surgical suite. The display screens 618, 620 may be coupled to the system 10 by a swinging hinge 617, as shown in FIGS. 31, 34, to allow the user and/or the support staff to be able to move the screen to a desired angle for improved visibility. In another embodiment, shown in FIG. 32, the operator display screen 618 may be coupled to the system 10 via a swivel hinge 619. The swivel hinge 619 is a multi-direction hinge providing the screen with greater mobility to allow the user to more easily position the screen 618.

Figure 35:
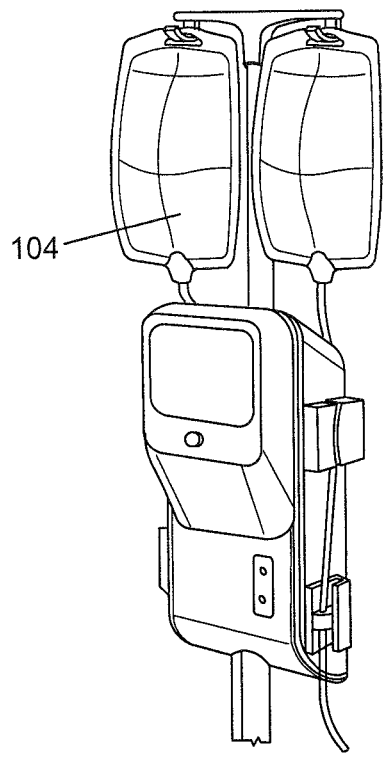
FIG. 35 shows a perspective view of a saline bag configuration according to an exemplary embodiment of the present disclosure.
Figure 36:
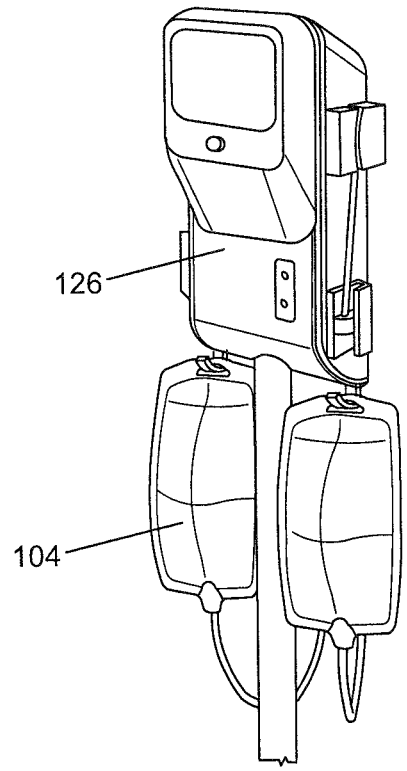
FIG. 36 shows a perspective view of a saline bag configuration according to another exemplary embodiment.
Figure 37:
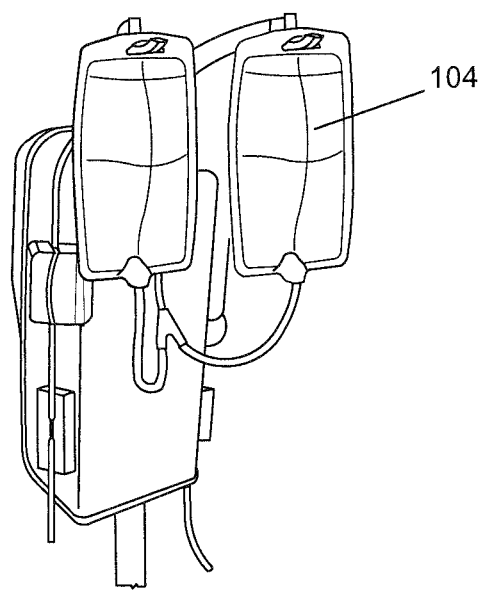
FIG. 37 shows a perspective view of a saline bag configuration according to a third exemplary embodiment.
Figure 38:
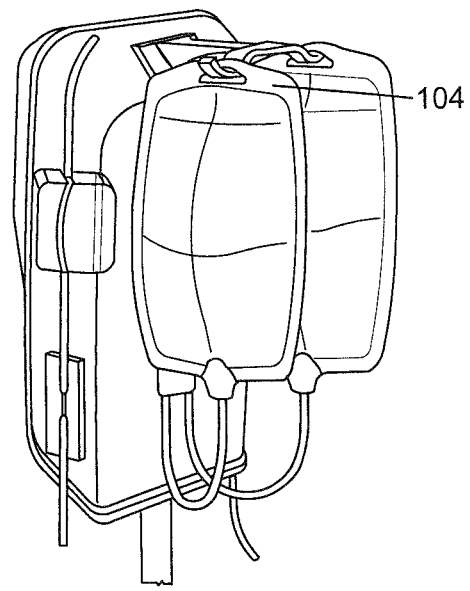
FIG. 38 shows a perspective view of a saline bag configuration according to a fourth exemplary embodiment.
Figure 39:
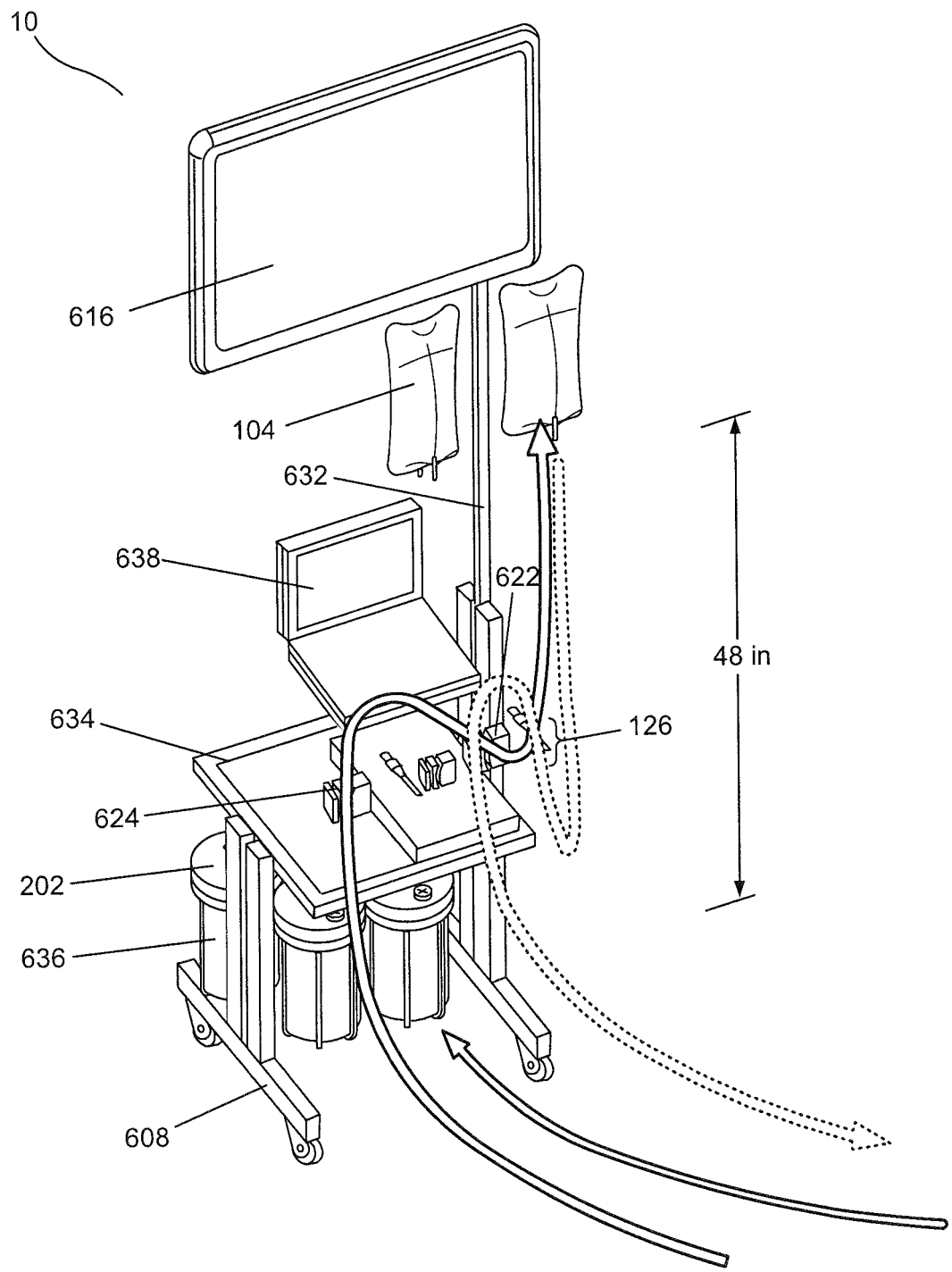
FIG. 39 shows a fluid management system modular cart configuration according to an exemplary embodiment of the present disclosure.

Positioning of the fluid saline bags 104 may also vary depending on loading, height, visualization and access preferences. In some cases, it may be preferable for the fluid bags 104 to be easily visible by the user. For example, a physician may wish to see the rate at which the saline is being used or the levels of saline that remain in each fluid bag 104 so as to know when the fluid bags 104 should be replaced. In another example, the procedure may require top or back access for a Y-pinch valve in the tubing. In these embodiments, shown in FIGS. 24-28 and 34, the fluid bags 104 may be mounted to the top of the IV pole. This high mounting allows the user or the support staff to easily see the fluid bags 104 while also allowing the tubing 136 to hang down for easy fluid flow. In one embodiment, shown in FIG. 28, where an external display is mounted to the top of the IV pole, the fluid bags 104 may be positioned behind the display. This rear access allows supporting staff to access the fluid bags 104 from behind the system 10 without interfering with the user's access to the modular components of the system 10. In another exemplary embodiment, the fluid bags 104 may be mounted to the bottom of the modular components of the system 10. For example, as shown in FIG. 35, the fluid bags 104 may be mounted to the bottom of the pumps 126. This embodiment includes the best loading access for the user/physician while also allowing good visibility of the fluid bags 104. In another exemplary embodiment shown in FIG. 36, the fluid bags 104 may be corner-mounted. That is, each of the fluid bags 104 may be mounted behind the modular systems at an angle. This configuration provides a good loading height and rear access for setup or changing of the bags by supporting staff. In another exemplary embodiment shown in FIG. 37, the fluid bags 104 may also be corner mounted. However, rather than being mounted at an angle, as in FIG. 36, the fluid bags 104 are mounted coaxially behind the modular systems. As with the embodiment of FIG. 36, this configuration provides supporting staff with a good loading height and rear access for easy setup and saline bag replacement. In some exemplary embodiments, the saline bag hanger may be a retracting hanger. For example, the arms of the hanger may be able to rotate/pivot inwards, pulling the bags closer to the main body. In another example, the arms themselves could telescope. This retracting hanger allows for ease of loading, in particular if multiple bags are being hung, and space minimizations.

In the vertical stack embodiments, the pumps 126 may be organized in vertical or horizontal groupings, or a combination thereof, as can be seen in FIGS. 24-34. That is, in a system 10 where the fluid management unit 100 includes multiple ingoing and/or outgoing pumps, the pumps 126 may be organized in different groupings to promote better fluid flow and provide different fluid flow pathways and efficiencies. For example, the Hi/Low flow outgoing pumps 622 may be vertically grouped or, as shown in FIGS. 24-26 and 28, the Hi/Low flow outgoing pumps 622 may be horizontally grouped. Similarly, the Hi/Low outgoing pumps 622 may be vertically grouped with an ingoing pump 624, or may be horizontally aligned with an ingoing pump 624, as in FIG. 27. Furthermore, in some embodiments, shown in FIGS. 27-28 the ingoing/outgoing pumps 624, 622 may have a symmetrical layout with respect to the entire system 10, with the ingoing pump 624 separated from the outgoing pumps. Alternatively, the ingoing and outgoing pumps 624, 622 may be positioned adjacent to one another, as depicted in FIGS. 24 and 26. In the exemplary embodiment of FIG. 24, the ingoing pump 624 may be disposed in a separate plane from the rest of the outgoing components, including the outgoing pumps 622. For example, the Hi/Lo outgoing pumps may be positioned on the front or a first side of the system while the ingoing pump is positioned on the opposite side of the system. In an exemplary embodiment, the Hi/Low outgoing pumps are retractable or are covered for proper setup. In each of the configurations of the pumps, the connections between the pumps and other modular components of the system 10 are grouped with the ingoing and outgoing pump sets.

Figure 30:
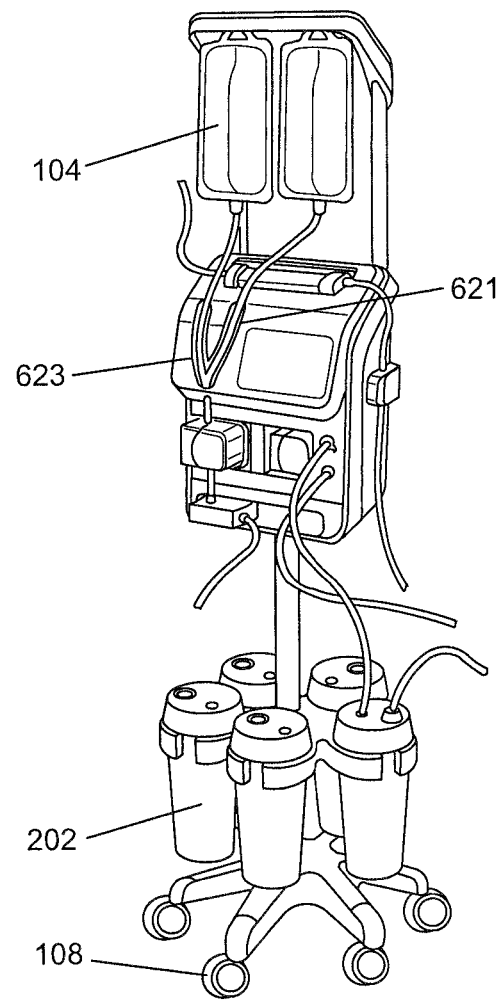
FIG. 30 shows a perspective view of a waste management system configuration according to a sixth exemplary embodiment.

In some embodiments of the vertically stacked fluid management system 10, various additional features may be integrated. For example, in one embodiment, shown in FIGS. 29-30, the system 10 may include a filter nests for the irrigation tubing extending from the patient. Filter nests are used to hold a cylindrical filter that filter fluid returning from the patient so it can be reused and pumped back into the patient. In other exemplary embodiments, shown in FIG. 30-31, the system 10 may include pinch valves to allow the user to stop the flow of saline from the fluid bags 104. In these embodiments, the fluid bags 104 are positioned directly over the rest of the system 10 to create a direct flow route from the fluid bags to, for example the pump system 126. In the embodiment of FIG. 30, a fluid bag hanger 102 may be angled forward from the pole 106 so that the fluid bags 104 hang in front of the unit, allowing for easier flow of the fluid, as well as greater visibility and access by the user.

In other exemplary embodiments shown in FIGS. 39-42, the fluid management system 10 may be positioned on a modular cart 630 including a rolling base 608. The modular cart 630 includes a pole 632 coupled to the side of the modular cart 630 and a flat clean top surface 634 for arranging the separate modular units. In one embodiment, shown in FIG. 39, the separate modular units may be vertically stacked. Specifically, the collection vessels 202 may be positioned at the bottom of the modular cart 630, beneath the flat surface 634. The collection vessels 202 may be snapped into covered vessel compartments 636 with exposed hookups (not shown) for connecting the collection vessels to the patient and the rest of the fluid management system 10. A folding touch screen 638 and the ingoing 624 and outgoing pumps 622 may be positioned on the clean top surface 634, with the ingoing 624 and outgoing pumps 622 separated by the touch screen 638. This layout is optimal for a compact modular cart and fluid management system 10. In this embodiment, the display unit 616 may be integrated with the modular cart 630 and coupled to the top of the pole 632 with the fluid bangs 104 hanging from the bottom of the display unit 616 for easy access by either the user or the support staff. Hanging the fluid bags 104 from the display unit 616 positions the bags 104 at a preferred loading height.

For example, the saline bags may be positioned at approximately 48 inches from the ground.

Figure 40:
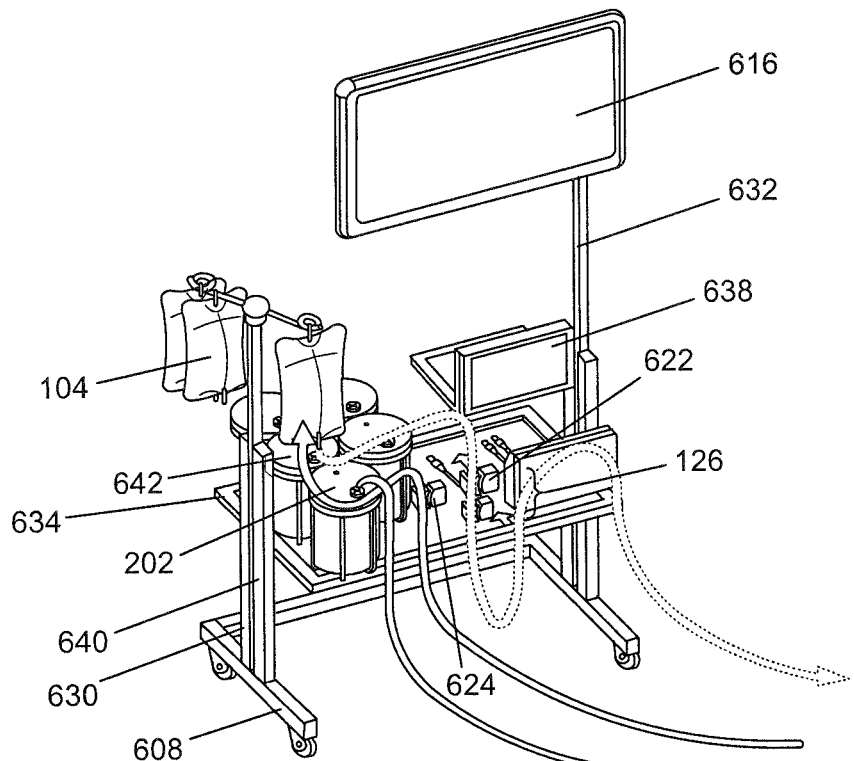
FIG. 40 shows a fluid management system modular cart configuration according to another exemplary embodiment.
Figure 41:
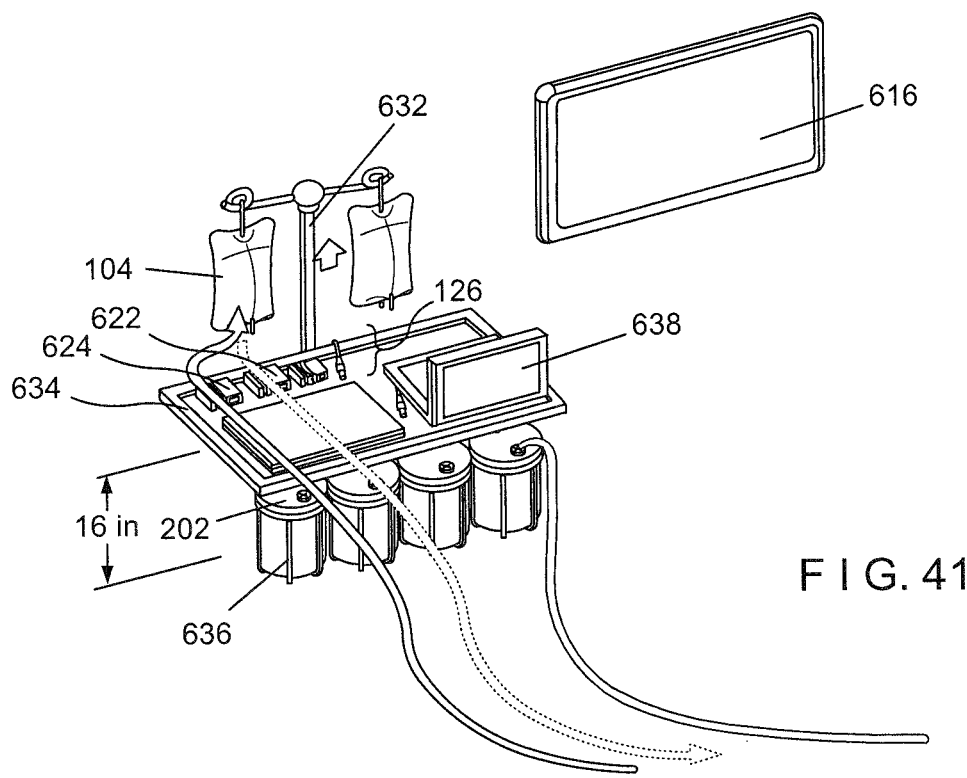
FIG. 41 shows a fluid management system modular cart configuration according to a third exemplary embodiment.

In another exemplary embodiment of the modular cart-based system, shown in FIG. 40, the separate modular functional units may be horizontally stacked on the clean top surface 634. The pole 632 may also be coupled to the side of the modular cart 630 in this embodiment, with fluid bags 104 hanging from the top of the pole 632. A second side pole 640 is positioned on the opposite side of the cart 634 for the display unit 616. The fluid bags 104 and the display unit 616 are positioned on opposing sides of the modular cart 630 to counterbalance one another to provide more stability to the modular cart 630. The ingoing 624 and outgoing 622 pumps may be arranged in vertical groupings on the flat top surface 634 with mechanical covers (not shown) or retracting mechanisms (not shown) for proper setups. Connections (not shown) are grouped with the ingoing 624 and outgoing 622 pump sets. The touch screen 638 may also be placed on the flat top surface 634. In this embodiment, the collection vessels 202 may be grouped in a covered compartment 642 disposed on the flat top surface 634, as shown in FIG. 40. This raised positioning of the collection vessels 202 on the flat top surface 634 enables easier observation and replacement of the collection vessels 202 within the compartment 642.

In some instances it may be beneficial to have a more compact modular cart setup. For example, a compact cart may be needed when there is very little available space in a surgical suite. In an exemplary embodiment of FIG. 41, a minimalist modular cart arrangement can be seen including a flat top surface 634 and a cart pole 632. The flat top surface 634, in this embodiment, may be positioned approximately 16 inches above the ground, providing just enough space therebelow for the collection vessels 202. The collection vessels 202 may be grouped in a front compartment 636 with exposed hookups (not shown) for connecting the collection vessels 202 to the rest of the fluid management system 10. The pole 632 in this embodiment is centrally located at the rear of the cart 630, with the fluid bags 104 hanging from a fluid bag hanger 102 at a top portion thereof for balance and to increase stability of the cart 630. All of the functional modular components—i.e., pumps, touch screen and connections—are positioned on the flat top surface 634 in a compact arrangement. Specifically, the ingoing 624 and outgoing 622 pumps are horizontally positioned and the touch screen 638 is a folding touch screen to promote a small cart layout. In order to make the cart layout as compact as possible, this embodiment uses a separate external display unit 616, which may be placed elsewhere in the room.

Figure 42:
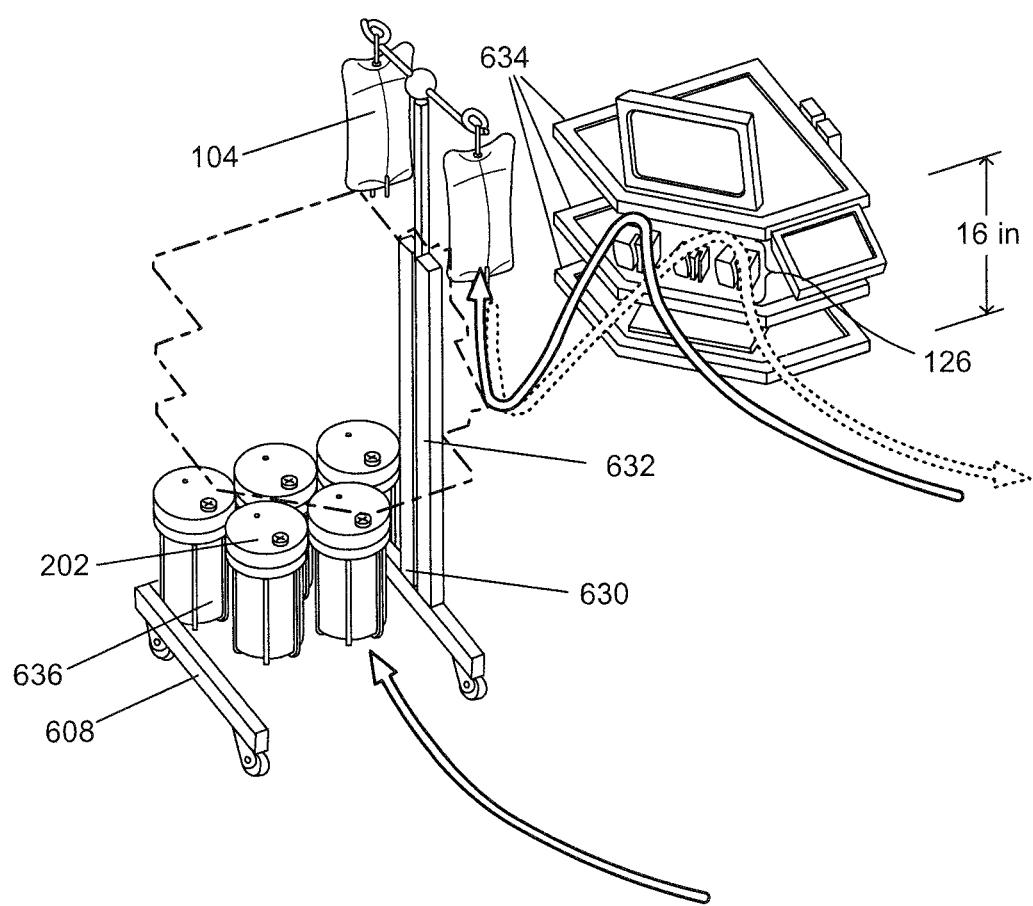
FIG. 42 shows a fluid management system modular cart configuration according to a fourth exemplary embodiment.

In another exemplary embodiment according to FIG. 42, a modular cart setup may include multiple stacking modules 644, which may be added or removed depending on the application. The modular cart 630, in this embodiment, includes the pole 632 for hanging fluid bags 104 and a collection vessel compartment 636 located at the bottom of the cart 630. Each of the modular devices or systems may be positioned on individual flat top surfaces 634, similar to shelves, which are configured to be coupled to the pole 632. For example, the touch screen 638 may be positioned on one removable flat top surface 634, the ingoing 624 and outgoing 622 pumps on a second flat top surface 634, and a heater on a third flat top surface 634. This removability of the flat top surfaces 634 increases the flexibility of the system 10, allowing the components of the system 10 to be changed depending on the patient or procedure. Furthermore, because the fluids can be managed on the cart 630, separate from the modular components of the system, accessibility is increased for supporting staff. The flat top surface may be connected to the pole via any suitable coupling mechanism. For example, the flat top surface may be mounted to the pole with screws or mounting hardware.

The fluid management system 10 may be an open loop system or a closed loop system. As previously noted, the fluid management system 10 is a modular system which allows addition, change or discontinuation of various modular components within the system 10. For example, the system 10 may be configured to include a heater assembly 138 for one application and subsequently, the heater assembly 138 may be removed for a different application. The touch screen interface 112 allows for addition and removal of various modular items so that feedback and alerts relating to each modular item is displayed to the user on the display screen 113.

Electrical power may be supplied to fluid management system 10 by any known method. For example, via a detachable cord. In an embodiment, some components may receive power from more than one power supply. For example, one or more power supply units may provide appropriate voltages and currents to the various electrical loads. The main processing device 124 may be protected by battery backup in case of power failure or accidental disconnection.

In an exemplary method of operating the fluid management system 10, a user may hang one or more fluid bags 104 on one or more of the weight sensor hooks 134 extending from the weight sensor 132. The fluid bags 104 are connected via a tube 136 to the peristaltic pumps 126. The pumps 126 may be connected via another tube 136 to the fluid flow inlet port 146 of the heater assembly 138. Another tube 136 may connect the fluid outlet port 148 of the heater assembly 138 to the scope device 20. The operator may then utilize touch screen interface 112 to set up the fluid management system 10, which may include selecting a surgical discipline (mode), procedure type, modular systems that are being used and set fluid pressure, temperature and flow rate set points, and/or other parameters (e.g., alarm set points, display content and/or arrangement). As the scope 20 is inserted into a target channel (i.e., bladder, ureter) within the patient, the user may start fluid circulation using the fluid flow on/off button 176 on the scope 20 or a touch button on the touch screen interface 112. Sensors positioned on the scope 20 provide feedback regarding conditions of the target anatomy in which the scope is positioned which is then displayed on the display screen 113. If the user has selected to put the system 10 in auto mode, changes in the pressure, temperature or visual feedback within by the sensors may automatically trigger a change in pump/flow rate if the change exceeds or is lower than a specific set point. Such a change may occur, for example, to improve visualization, flush out blood, urine, blood clots or debris or, in the event that a tool has been inserted through the scope, to compensate for the reduced flow space within the working channel. Simultaneously, the user and/or the entire surgical team may be alerted of this change by an audio or visual alert. Once the sensors detect that conditions have normalized (i.e., obstruction or tool has been removed), the system 10 will reduce the pump/flow rate. At any point in the procedure, the user may switch the system 10, via the touch screen interface 112 or other physical switch, so that components thereof, such as the pump 126, may be adjusted manually. Manual adjustment may occur through use of a foot pedal 117 or through touch buttons on the display screen 113.

Contemporaneously, the various other modular devices and systems, such as the heater assembly 138, the pumps 126 and the fluid deficit monitoring system 130, may also provide information for the user on the display screen 113 regarding the operating conditions of each system. For example, the heater assembly may display the internal temperature of the heater and the fluid flowing through the heater assembly 138. In another example, the pumps 126 may provide a pump rate to the display screen and the fluid deficit system may provide the amount of time remaining before an existing fluid bag 104 should be replace, as previously discussed. The user may switch the system 10 to manual mode at any time control each of the modular systems manually.

It will be appreciated by those skilled in the art that the current devices and methods are not limited to the disclosed embodiments. For example, the disclosed fluid management system 10 may be used in various other procedures such as, for example, hysteroscopies, cystoscopies, TURP, etc. Thus, the system 10 is not limited to use with a ureteroscope but may be used with other devices such as cystoscopes, hysteroscopes or any other device with sensor and image capability.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A fluid management system, comprising:
a pump configured to pump a fluid from a fluid supply source through the fluid management system at a fluid flow rate;
a processor including a user interface, the user interface allowing a user to input a set of system operating parameters, the processor determining a target therapeutic flow rate based on the set of system operating parameters, the processor being configured to control the pump to maintain the fluid flow rate within a target therapeutic fluid flow range based on the target therapeutic flow rate, the processor receiving video feedback relating to a target surgical site; and
a scope device coupled to the pump to deliver the fluid to the target surgical site, the scope device including a flexible elongated shaft extending from a distal end of the scope device, the flexible elongated shaft including at least two sensors at a distal portion of the flexible elongated shaft so that, when the distal portion of the flexible elongated shaft is positioned adjacent to the target surgical site, the at least two sensors are positioned within a body lumen adjacent to the target surgical site, the at least two sensors transmitting sensor data relating to the target surgical site to the processor,
wherein the processor automatically signals to the pump to adjust from pumping the fluid at the target therapeutic flow rate to pumping the fluid at a different flow rate for a predetermined time period based on the video feedback, wherein at an end of the predetermined time period, the processor is configured to automatically signal to the pump to revert to pumping the fluid at the target therapeutic flow rate.

2. The system of claim 1, wherein one of the at least two sensors is a pressure sensor.

3. The system of claim 1, further comprising a heating assembly, the heating assembly configured to heat the fluid to a target temperature.

4. The system of claim 1, wherein the processor further includes a display screen configured to display the fluid flow rate and the sensor data in real time.

5. The system of claim 4, wherein if the processor detects that the fluid flow rate is outside of the target therapeutic fluid flow range, a visual alert is displayed on the display screen.

6. The system of claim 1, wherein one of the at least two sensors is a temperature sensor.

7. The system of claim 1, wherein the fluid supply source is a fluid bag.

8. The system of claim 1, further comprising a weight sensor for measuring a weight of the fluid supply source in real time.

9. The system of claim 1, wherein each of the target therapeutic flow rate and the different flow rate is greater than zero.

10. A fluid management system, comprising:
a pump configured to pump a fluid from a fluid supply source through the fluid management system at a first fluid flow rate selected for a therapeutic purpose;
a processor configured to control the pump; and
a scope device coupled to the pump to deliver the fluid to a target surgical site, the scope device including an elongated shaft extending from a distal end thereof, the elongated shaft including a camera, the camera transmitting video feedback relating to the target surgical site to the processor,
wherein the processor includes image recognition software to detect variations in brightness or color pixilation in the video feedback and automatically signals to the pump to adjust from pumping the fluid at the first fluid flow rate to pumping the fluid at a second fluid flow rate for a predetermined time period based on the variations in the brightness or the color pixilation to improve images from the camera, wherein at an end of the predetermined time period, the pump is configured to revert to pumping the fluid at the first fluid flow rate.

11. The system of claim 10, wherein the processor includes a user interface allowing a user to input a set of system operating parameters.

12. The system of claim 10, wherein the processor includes a display screen configured to display the video feedback and at least one of the first fluid flow rate or the second fluid flow rate in real time.

13. The system of claim 10, wherein the scope device further includes a temperature sensor located on the elongated shaft.

14. The system of claim 10, further comprising a heating assembly, the heating assembly configured to heat the fluid to a target temperature.

15. The system of claim 10, wherein the fluid supply source is a fluid bag.

16. The system of claim 10, further comprising a weight sensor for measuring a weight of the fluid supply source in real time.

17. The system of claim 10, wherein each of the first fluid flow rate and the second fluid flow rate is greater than zero.

* * * * *